US006168917B1

(12) United States Patent
Kilpatrick

(10) Patent No.: US 6,168,917 B1
(45) Date of Patent: Jan. 2, 2001

(54) DETECTION AND IDENTIFICATION OF NON-POLIO ENTEROVIRUSES

(75) Inventor: David Kilpatrick, Norcross, GA (US)

(73) Assignee: The United States of America as represented by the Department of Health and Human Services, Washington, DC (US)

( * ) Notice: Under 35 U.S.C. 154(b), the term of this patent shall be extended for 0 days.

(21) Appl. No.: 09/147,933

(22) PCT Filed: Oct. 1, 1997

(86) PCT No.: PCT/US97/17734

§ 371 Date: Jul. 9, 1999

§ 102(e) Date: Jul. 9, 1999

(87) PCT Pub. No.: WO98/14611

PCT Pub. Date: Apr. 9, 1998

Related U.S. Application Data

(60) Provisional application No. 60/027,353, filed on Oct. 2, 1996.

(51) Int. Cl.[7] .............................. C12Q 1/70; C12P 19/34; C07H 21/04

(52) U.S. Cl. .................................. 435/5; 435/5; 435/91.2; 435/235.1; 536/24.33; 536/24.31; 536/24.32

(58) Field of Search .............................. 536/24.33, 24.31, 536/24.32; 435/235.1, 5, 91.2

(56) References Cited

FOREIGN PATENT DOCUMENTS

WO 90/11376 * 10/1990 (WO).

OTHER PUBLICATIONS

Egger, et al. "Reverse Transcription Multiplex RCR for Differentiation between Polio and Enteroviruses from Clinical and Environmental Samples" J of Clinical Micro. 33(6):1442–1447.*

* cited by examiner

Primary Examiner—W. Gary Jones
Assistant Examiner—B. J. Forman
(74) Attorney, Agent, or Firm—Fitch, Even, Tabin & Flannery

(57) ABSTRACT

This invention provides sensitive nucleic acid hybridization assay methods for the detection of non-polio enterovirus nucleic acids. The methods are particularly useful in detecting the presence of enterovirus nucleic acids in a biological sample and for ascertaining the serotype of enteroviruses present in a sample.

13 Claims, 8 Drawing Sheets

QUICK SCREEN CHART FOR NPEV PRIMER POOL*

```
1  2  3  4  5  6  7  8
-  -  -  -  -  -  -  -   =A12, A21, A24, EV68
-  -  -  -  -  +  -  -   =A14
-  -  -  -  -  +  +  -   =A3
-  -  -  -  +  -  +  -   =A4, A5, A6, EV70
-  -  -  -  +  +  +  -   =A8
+  -  -  -  -  -  -  -   =A9, EC18
-  -  -  -  +  +  -  -   =A10, A16, EV71
+  +  +  +  -  -  -  -   =B1, B2, B3, B4, B5, B6, EC4, EC30
+  +  +  +  -  -  +  +   =EC11
+  +  +  +  -  -  -  +   =EC19
+  +  +  +  -  -  +  -   =EC24
+  +  -  +  -  -  -  -   =EC3, EC27
+  +  -  +  -  -  +  +   =EC17
+  +  -  +  -  -  +  -   =EC13
+  -  +  -  -  -  -  -   =EC14
+  -  +  +  -  -  -  -   =EC20, EC25, EC32, EC33
+  -  +  +  -  -  +  +   =EC12, EC21, EC29
+  -  -  +  -  -  +  +   =EC31
+  -  -  +  -  -  -  -   =EC15, EC16, EC26
+  -  -  +  -  -  +  -   =EV69
-  +  +  +  -  -  -  -   =EC6, EC7
-  -  +  +  -  -  +  -   =EC9
-  -  -  +  -  -  -  -   =EC5, EC8
```

*LANE 1=5S/6A; 2=7S/9A; 3=14S/11A; 4=51S/52A; 5=61S/68A; 6=64S/65A; 7=67S/1A; 8=67S/8A.

Fig. 2A

NPEV VP1 AMINO ACID ALLIGNMENT

```
A)
CAV24   GIEETIDTVISNALQLSQPKPQKQLTAQSTPSTS....GVNSQEVPALTAVETGVSGQAIPSDVIETRHVVNYKTRSESTL
CAV21   GIEDLIDTAIKNALRVSQPLRPSQLKQ.........PNGVNSQEVPALTAVETGASGQAIPSDVVETRHVINYKTRSESCL
CAV16   GDGIADMIDQAVTSRVGRALTSLQVEPTAANTNASE.HRLGTGLVPALQAAETGASSNAQDENLIETRCVLNHHSTQETTI
CAV2    GDGIEDAITNTVNATINRVLDRPISHSSTAANTQVSQHSIETGRVPALQAAETGATSNASDENLIETRCVVNKNSVEEASL
CAV9    GDVEEAIERARCTVADTMRTGPS.................NSASVPALTAVETGHTSQVTPSDTMQTRHVKNYHSRSESTV
CBV1    GPVEESVERAMVRVADTVSSKPT.................NSESIPALTAAETGHTSQVVPSDTMQTRHVKNYHSRSESSI
CBV3    GPVEDAITAAIGRVADTVGTGPT.................NSEAIPALTAAETGHTSQVVPGDTMQTRHVKNYHSRSESTI
CBV4    GPTEESVERAMGRVADTIARGPS.................NSEQIPALTAVETGHTSQVDPSDTMQTRHVHNYHSRSESSI
CBV5    GPPGEAVERAIARVADTISSGPV.................NSESIPALTAAETGHTSQVVPADTMQTRHVKNYHSRSESTV
ECHO6   NDVQNAVERSIVRVADTLPSGPS.................NSESIPALTAAETGHTSQVVPSDTIQTRHVRNFHVRSESSV
ECHO9   SDVREAVEGAIGRVADTIRSGPS.................NSEAVPALTAAETGHTSQVVPSDTMQTRHVKNYHSRSESTI
ECHO11  GDVVEAVENAVARVADTIGSGPS.................NSQAVPALTAVETGHTSQVTPSDTMQTRHVKNYHSRSESSI
ECHO12  GDVEEAVNRAVARVADTLPTGPR.................NSESIPALTAAETGHTSQVVPGDTMQTRHVKNYHSRTESSV
EV70    GEIVKTVANTVE......................SEIKAELGVIPSLNAVETGATSNTEPEEAIQTRTVINMHGTAECLV
EV71    GDRVADVIESSIGDSVSRALTQALPAPTGQNTQVS.SHRLDTGEVPALQAAEIGASSNTSDESMIETRCVLNSHSTAETTL
```

Fig. 2B

```
CAV24   ESFFGRSACVTMLEVENFNATTEADKKKQFTTWAITYTDTVQL..RRKLEFFTYSRFDLEMTFVITERYYTSNT..GYARNQVYQ
CAV21   ESFFGRAACVTILSLTNSSKSGEE..KKHFNIWNITYTDTVQL..RRKLEFFTYSRFDLEMTFVFTENYPSTAS..GEVRNQCDQ
CAV16   GNFFSRAGLVSIITMPTTGTQNTDGY.....VNWDIDLMGYAQM.RRKCELFTYMRFDAEFTFVAAKPN.......GELVPQLLQ
CAV2    NHFFSRAALVGKVELNDTGTAATGFT.....NWNIDIMGYAQL.....RRKLEMFTYMRFNAEFTFVATTRA......GRVPSRVLQ
CAV9    ENFLGRSACVYMEEYKTDKHVN...KKF.VAWPINTKQMVQM.RRKLEMFTYLRFDMEVTFVITSRQDPGTTLAQDMPVLTRQ
CBV1    ENFLCRSACVYYATYNNNSEKG...YAE....WVINTRQVAQLLRRKLEF.TYLRFDLELTFVITSAQEPSTATSVDAPVQTQQ
CBV3    ENFLCRSACVYFTEYKNSGAKR...YAE....WVLTPRQAAQL.RRKLEFFTYVRFDLELTFVITSTQQPSTTQNQDAQILTHQ
CBV4    ENFLCRSACVYIKYSSAESNNLKRYAE....WVINTRQVAQL.RRKMEMFTYIRCDMELTFVITSHQEMSTATNSDVPVQTHQ
CBV5    ENFLCRSACVYYTTYKNHGTDGNFAY......WVINTRQVAQL.RRKLEMFTYARFDLELTFVITSTQEQSTIQGQDSPVLTHQ
ECHO6   ENFLSRSACVYIVEYKTQDTTPD....KMYDSWVINTRQVAQL.RRKLEFFTYVRFDVEVTFVITSVQDDSTRQNTDTPVLTHQ
ECHO9   ENFLCRSACVYRMAKYEARGNLKA....LTLDAWEISVRDMVQL.RRKCEMFTYLRFDVEVTFVITSYQRQGTSSIQICPYDAHQ
ECHO11  ENFLSRSACVYMGGYHTTNTDQT....KLFASWTISARRMVQM.RRKLEIFTYVRFDVEVTFVITSKQDQGSRLGQDMPPLTHQ
ECHO12  ENFLCRAACVCITKYTKDSDPV....QRYANWRINTRQMAQL.RRKFELFTYLRFDMEVTFVITSSQDDGTQLAQDMPVLTHQ
EV70    ENFLGRSALVCMRSFEYKNHSTSTSSIQKNFFVWTLNTRELVQIRRKMELFTYLRFDTEITIVPTLRLFSSSNASSSGLPNLTLQ
EV71    DSFFSRAGLVGEIDLPL... EGTTNPNGYANWDIDITGYAQ.MRRKVELFTYMRFDAEFTFV......ACTPTGEVVP.QLLQ
```

Fig. 2C

B)
```
CAV24   LMYIPPGAPRPTAWDDYTWQSSSNPSVFYTYGSAPPRISIPYVGIANAYSHFYDGFARVPLKDETVDSGDTYYGLVTI
CAV21   IMYIPPGAPRPSSWDDYTWQSSSNPSIFYMYGNAPPRMSIPYVGIANAYSHFYDGFARVPLEGENTDAGDTFYGLVSI
CAV16   YMVVPPGAPKPTSRDSFAWQTATNPSIFVKLTDPPAQVSVPFMSPASAYQWFYDGYPTFGAHPQSNDADYGQCP....
CAV2    YMVPPGAPKPDGREAFQWQSSTNPSVFSKMTDPPPQVSVPFMSPASAYHGFYDGYPTFGEHNGEDSLRTGNA.....
CAV9    IMYVPPGGPIPAKVDDYAWQTSTNPSIFWTEGNAPARMSIPFISIGNAYSNFYDGWSNFDQRGSYGYNTL........
CBV1    IMYVPPGGPVPTKVTDYAWQTSTNPSVFWTEGNAPPRMSIPFISIGNAYSCFYDGWTQFSRNGVYGINTL........
CBV3    IMYVPPGGPVPDKVDSYVWQTSTNPSVFWTEGNAPPRMSIPFLSIGNAYSNFYDGWSEFSRNGVYGINTL........
CBV4    IMYVPPGGPVPTSVNDYVWQTSTNPSIFWTEGNAPPRMSIPFMSIGNAYTMFYDGWSNFSRDGIYGYNSL........
CBV5    IMYVPPGGPVPTKINSYSWQTSTNPSVFWTEGSAPPRISIPFISIGNAYSMFYDGWAKFDKQGTYGINTL........
ECHO6   IMYVPPGGPIPHAVDDYNWQTSTNPSVFWTEGNAPPRMSIPFMSVGNAYSNFYDGWSHFSQTGVYGFNTL........
ECHO9   IMYIPPGGPIPKKVDGYEWQTSTNPSIFWTEGNAPPRMSIPFISIGNAYSSFYDGWSHFDSKGAYGFNTL........
ECHO11  IMYIPPGGPIPKSVTDYAWQTSTNPSIFWTEGNAPPRMSIPFISIGNAYSNFYDGWSHFSQNGVYGYNTL........
ECHO12  VMYIPPGGPVPNSATDFAWQSSTNPSIFWTEGNAPARMSIPFISIGNAYSNFYDGWSHFTQDGVYGFNSL........
EV70    VMYVPTGAPKPSSQDSFEWQSACNPSVFFKINDPPARLTIPFMSINSAYANFYDGFAGFEKKAT..DL....YGINPA
EV71    YMFVPPGAPKPESRESLAWQTATNPSVFVKLTDPPAQVSVPFMSPASAYQWFYDGYPTFGEHKQEKDLE...YGACP.
```

Fig. 2D

```
CAV24   NDFGTLAVRVVNEFNPARIISKIRVYMKPKHVRCWCPRPPRAVPY.RGEGVDFKQDSITPLIAVEN.INTF..................
CAV21   NDFGVLAVRAVNRSNPHTIHTSVRVYMKPKHIRCWCPRPPRAVLY.RGEGVDMISSAIQPLTKVDS.ITTF..................
CAV16   NNMMGTFSIRTVGTEKSPHSITLRVYMRIKHVRAWIPRPLRNQPYLFKTNPNYKGNDIKCTSTSRDKITTL..................
CAV2    NNALGTFSVRFVSEEITNERIIRIYMRLKHIRAWVPRPLRSEPYVLKNFPNYTAVTHVTANRPSITNTGRF..................
CAV9    NNLGHIYVRHVSGSSPHPITSTIRVYFKPKHTRAWVPRPPRLCQYKKAFSVDFTPTPITDTRKD...INTVAQSRRRGDMSTLNTHGAF
CBV1    NNMGTLYMRHVNEAGQGPIKSTVRIYFKPKHVKAWVPRPPRLCQYEKQKNVNFNPTGVTTRSN...ITTT..................
CBV3    NNMGTLYARHVNAGSTGPIKSTIRIYFKPKHVKAWIPRPPRLCQYEKAKNVNFQPSGVTTRQS...ITTM..................
CBV4    NNMGTIYARHVNDSSPGGLTSTIRIYFKPKHVKAYVPRPPRLCQYKKAKSVNFDVEAVTAERAS..LITT..................
CBV5    NNMGTLYMRHVNDGSPGPIVSTVRIYFKPKHVKTWVPRPPRLCQYQKAGNVNFEPTGVTESRTE..ITAM..................
ECHO6   NNMGKLYFRHVNDRTISPITSKVRIYFKPKHVKAWVPRPPRLCEYTHKDNVDYEPKGVTTSRTS..ITITNSKHMETHGAF........
ECHO9   NKMGHIYCRHVNKETPTKVTSYIRIYFKPKHVRAWVPRPPRLCQYMNKANVNFEATAVTDTRDT..INTVPLSTHGVSRGAY.......
ECHO11  NHMGQIYVRHVNGSSPLPMTSVRMYFKPKHVKAWVPRPPRLCQYKNASTVNFTPTNVTDKRTS...INYIPE.................
ECHO12  NNMGSIYIRHVNEQSPYAITSTVRVYFKPKHVRAWVPRPPRLCAYEKSSNVNFKPTDVTTSRTS..ITEVPS.................
EV70    NTMGNLCLRVVNSYQPVQYTLTVRVYMKPKHIKAWAPRAPRTMPYTNILNNNYVGRSAAPNAPTAIVSDRSTIKTMPNDIDLTTA....
EV71    NNMMGTFSVRTVGSSKSKYPLVVRIYMRMKHVRAWIPRPMRNQNYLFKANPNYTGNSIKPTGTSR...........NAITTL......
```

Fig. 3

NPEV PCR PRIMER POOL

| PRIMERS | SIZE(BP) | A9 | A12 | A21 | B1 | B2 | B3 | B4 | B5 | B6 | EC4 | EC11 | EC30 | EV71 |
|---|---|---|---|---|---|---|---|---|---|---|---|---|---|---|
| 5S/6A* | 101 | + | - | - | + | + | + | + | + | + | + | + | + | - |
| 6S/7A | 134 | + | - | - | + | + | + | + | + | + | + | + | - | - |
| 7S/8A | 143 | - | - | - | - | - | + | + | + | - | - | - | - | - |
| 7S/9A* | 107 | - | - | - | + | + | + | + | + | + | + | + | + | - |
| 14S/11A* | 130 | - | - | - | + | + | + | + | + | + | + | + | + | - |
| 24S/47A | 77 | + | - | - | + | + | + | - | + | + | - | - | + | - |
| 24S/25A | 98 | + | - | - | - | + | - | - | - | - | - | - | - | - |
| 24S/46A | 98 | + | - | - | + | + | + | - | - | + | - | - | - | - |
| 34S/28A | 86 | - | - | + | - | - | - | - | - | - | - | - | - | - |
| 34S/33A | 89 | - | - | - | + | - | - | + | + | + | - | - | - | - |
| 34S/35A | 104 | - | - | - | - | - | - | - | - | + | - | + | - | - |
| 34S/38A | 101 | - | - | - | - | - | - | - | - | - | - | + | - | - |
| 34S/73A | 98 | + | - | - | - | - | - | - | - | - | - | + | - | - |
| 36S/35A | 80 | - | - | - | - | - | - | - | - | - | - | + | - | - |
| 39S/40A | 71 | - | + | - | - | - | - | - | - | - | - | - | - | + |
| 39S/41A | 62 | - | - | - | - | - | - | - | - | - | - | - | - | + |
| 51S/52A* | 83 | - | - | - | + | + | + | + | + | + | + | + | + | - |
| 55S/54A | 140 | - | - | - | - | - | - | - | - | - | - | - | - | + |
| 59S/27A | 152 | - | - | - | - | - | - | - | - | - | - | - | - | - |
| 61S/68A* | 104 | - | - | - | - | - | - | - | - | - | - | - | - | + |
| 62S/27A | 131 | - | - | - | - | - | - | - | - | - | - | - | - | - |
| 63S/43A | 80 | - | - | - | - | - | - | - | - | - | - | - | - | - |
| 64S/69A | 180 | - | - | - | - | - | - | - | - | - | - | - | - | - |
| 64S/65A* | 166 | - | - | - | - | - | - | - | - | - | - | - | - | + |
| 67S/1A* | 155 | - | - | - | - | - | - | - | - | - | - | + | - | - |
| 67S/8A* | 1147 | - | - | - | - | - | - | - | - | - | - | + | - | - |

*=PRIMERS SELECTED FOR SCREENING COMPLETE NPEV COLLECTION

Fig. 4  NPEV PCR PRIMER POOL

| EV | 5S/6A | 7S/9A | 14S/11A | 51S/52A | 61S/68A | 64S/65A | 67S/1A | 67S/8A |
|---|---|---|---|---|---|---|---|---|
| A3 | - | - | - | - | + | - | + | - |
| A4 | - | - | - | - | + | - | - | - |
| A5 | - | - | - | - | + | - | - | - |
| A6 | - | - | - | - | + | - | - | - |
| A8 | - | - | - | - | + | + | + | - |
| A9 | + | - | - | - | - | - | - | - |
| A10 | - | - | - | - | + | + | - | - |
| A12 | - | - | - | - | - | - | - | - |
| A14 | - | - | - | - | - | + | - | - |
| A16 | - | - | - | - | + | + | - | - |
| A21 | - | - | - | - | - | - | - | - |
| A24 | - | - | - | - | - | - | - | - |
| B1 | + | + | + | + | - | - | - | - |
| B2 | + | + | + | + | - | - | - | - |
| B3 | + | + | + | + | - | - | - | - |
| B4 | + | + | + | + | - | - | - | - |
| B5 | + | + | + | + | - | - | - | - |
| B6 | + | + | + | + | - | - | - | - |
| EC3 | + | + | - | + | - | - | - | - |
| EC4 | + | + | + | + | - | - | - | - |
| EC5 | - | - | - | + | - | - | - | - |
| EC6 | - | + | + | + | - | - | - | - |
| EC7 | - | + | + | + | - | - | - | - |
| EC8 | - | - | - | + | - | - | - | - |
| EC9 | - | - | + | + | - | - | + | - |
| EC11 | + | + | + | + | - | - | + | + |
| EC12 | + | - | + | + | - | - | + | + |
| EC13 | + | + | - | + | - | - | + | - |
| EC14 | + | - | + | - | - | - | - | - |
| EC15 | + | - | - | + | - | - | - | - |
| EC16 | + | - | - | + | - | - | - | - |
| EC17 | + | + | - | + | - | - | + | + |
| EC18 | + | - | - | - | - | - | - | - |
| EC19 | + | + | + | + | - | - | - | + |
| EC20 | + | - | + | + | - | - | - | - |
| EC21 | + | - | + | + | - | - | + | + |
| EC24 | + | + | + | + | - | - | + | - |
| EC25 | + | - | + | + | - | - | - | - |
| EC26 | + | - | - | + | - | - | - | - |
| EC27 | + | + | - | + | - | - | - | - |
| EC29 | + | - | + | + | - | - | + | + |
| EC30 | + | + | + | + | - | - | - | - |
| EC31 | + | - | - | + | - | - | + | + |
| EC32 | + | - | + | + | - | - | - | - |
| EC33 | + | - | + | + | - | - | - | - |
| EV68 | - | - | - | - | - | - | - | - |
| EV69 | + | - | - | + | - | - | + | - |
| EV70 | - | - | - | - | + | - | - | - |
| EV71 | - | - | - | - | + | + | - | - |

Fig. 5

QUICK SCREEN CHART FOR NPEV PRIMER POOL*

| 1 | 2 | 3 | 4 | 5 | 6 | 7 | 8 |   |
|---|---|---|---|---|---|---|---|---|
| − | − | − | − | − | − | − | − | =A12, A21, A24, EV68 |
| − | − | − | − | − | + | − | − | =A14 |
| − | − | − | − | + | − | + | − | =A3 |
| − | − | − | − | + | − | − | − | =A4, A5, A6, EV70 |
| − | − | − | − | + | + | + | − | =A8 |
| + | − | − | − | − | − | − | − | =A9, EC18 |
| − | − | − | − | + | + | − | − | =A10, A16, EV71 |
| + | + | + | + | − | − | − | − | =B1, B2, B3, B4, B5, B6, EC4, EC30 |
| + | + | + | + | − | − | + | + | =EC11 |
| + | + | + | + | − | − | − | + | =EC19 |
| + | + | + | + | − | − | + | − | =EC24 |
| + | + | − | + | − | − | − | − | =EC3, EC27 |
| + | + | − | + | − | − | + | + | =EC17 |
| + | + | − | + | − | − | + | − | =EC13 |
| + | − | + | − | − | − | − | − | =EC14 |
| + | − | + | + | − | − | − | − | =EC20, EC25, EC32, EC33 |
| + | − | + | + | − | − | + | + | =EC12, EC21, EC29 |
| + | − | − | + | − | − | + | + | =EC31 |
| + | − | − | + | − | − | − | − | =EC15, EC16, EC26 |
| + | − | − | + | − | − | + | − | =EV69 |
| − | + | + | + | − | − | − | − | =EC6, EC7 |
| − | − | + | + | − | − | + | − | =EC9 |
| − | − | − | + | − | − | − | − | =EC5, EC8 |

*LANE 1=5S/6A; 2=7S/9A; 3=14S/11A; 4=51S/52A; 5=61S/68A; 6=64S/65A; 7=67S/1A; 8=67S/8A.

SEQUENCE LISTING

<160> NUMBER OF SEQ ID NOS: 96

<210> SEQ ID NO 1
<211> LENGTH: 7
<212> TYPE: PRT
<213> ORGANISM: Artificial Sequence
<220> FEATURE:
<223> OTHER INFORMATION: peptide

<400> SEQUENCE: 1

Phe Gly Gln Gln Ser Gly Ala
 1               5

<210> SEQ ID NO 2
<211> LENGTH: 7
<212> TYPE: PRT
<213> ORGANISM: Artificial Sequence
<220> FEATURE:
<223> OTHER INFORMATION: peptide

<400> SEQUENCE: 2

Met Tyr Val Pro Pro Gly Gly
 1               5

<210> SEQ ID NO 3
<211> LENGTH: 7
<212> TYPE: PRT
<213> ORGANISM: Artificial Sequence
<220> FEATURE:
<223> OTHER INFORMATION: peptide

<400> SEQUENCE: 3

Trp Thr Glu Gly Asn Ala Pro
 1               5

<210> SEQ ID NO 4
<211> LENGTH: 6
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: "RESIDUE 2 = THR OR SER"
<223> OTHER INFORMATION: peptide

<400> SEQUENCE: 4

Asn Xaa Leu Asn Asn Met
 1               5

<210> SEQ ID NO 5
<211> LENGTH: 7
<212> TYPE: PRT
<213> ORGANISM: Artificial Sequence
<220> FEATURE:
<221> NAME/KEY: VARIANT
<222> LOCATION: (5)...(5)
<223> OTHER INFORMATION: "RESIDUE 5 = TYR OR GLN"
<223> OTHER INFORMATION: peptide

<400> SEQUENCE: 5

Gly Ala Thr Gly Xaa Gln Ser
 1               5

<210> SEQ ID NO 6
<211> LENGTH: 7
<212> TYPE: PRT

```
<213> ORGANISM: Artificial Sequence
<220> FEATURE:
<223> OTHER INFORMATION: peptide

<400> SEQUENCE: 6

Phe Lys Pro Lys His Val Lys
 1               5

<210> SEQ ID NO 7
<211> LENGTH: 7
<212> TYPE: PRT
<213> ORGANISM: Artificial Sequence
<220> FEATURE:
<223> OTHER INFORMATION: peptide

<400> SEQUENCE: 7

Thr Met Gln Thr Arg His Val
 1               5

<210> SEQ ID NO 8
<211> LENGTH: 7
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: "RESIDUE 2 = MET OR ILE"
<220> FEATURE:
<221> NAME/KEY: VARIANT
<222> LOCATION: (3)...(3)
<223> OTHER INFORMATION: " RESIDUE 3 = GLY OR VAL"
<223> OTHER INFORMATION: peptide

<400> SEQUENCE: 8

Ala Xaa Xaa Arg Val Ala Asp
 1               5

<210> SEQ ID NO 9
<211> LENGTH: 7
<212> TYPE: PRT
<213> ORGANISM: Artificial Sequence
<220> FEATURE:
<221> NAME/KEY: VARIANT
<222> LOCATION: (6)...(6)
<223> OTHER INFORMATION: "RESIDUE 6 = ALA OR VAL"
<223> OTHER INFORMATION: peptide

<400> SEQUENCE: 9

Pro Ala Leu Thr Ala Xaa Glu
 1               5

<210> SEQ ID NO 10
<211> LENGTH: 7
<212> TYPE: PRT
<213> ORGANISM: Artificial Sequence
<220> FEATURE:
<221> NAME/KEY: VARIANT
<222> LOCATION: (3)...(3)
<223> OTHER INFORMATION: "RESIDUE 3 = LYS OR HIS"
<220> FEATURE:
<221> NAME/KEY: VARIANT
<222> LOCATION: (4)...(4)
<223> OTHER INFORMATION: "RESIDUE 4 = SER OR THR"
<223> OTHER INFORMATION: peptide

<400> SEQUENCE: 10

Asn Tyr Xaa Xaa Arg Ser Glu
 1               5
```

```
<210> SEQ ID NO 11
<211> LENGTH: 7
<212> TYPE: PRT
<213> ORGANISM: Artificial Sequence
<220> FEATURE:
<223> OTHER INFORMATION: peptide

<400> SEQUENCE: 11

Pro Ala Leu Thr Ala Val Glu
 1               5

<210> SEQ ID NO 12
<211> LENGTH: 6
<212> TYPE: PRT
<213> ORGANISM: Artificial Sequence
<220> FEATURE:
<223> OTHER INFORMATION: peptide

<400> SEQUENCE: 12

Gly Glu Val Arg Asn Gln
 1               5

<210> SEQ ID NO 13
<211> LENGTH: 7
<212> TYPE: PRT
<213> ORGANISM: Artificial Sequence
<220> FEATURE:
<223> OTHER INFORMATION: peptide

<400> SEQUENCE: 13

Gln Asn Gln Asp Ala Gln Ile
 1               5

<210> SEQ ID NO 14
<211> LENGTH: 7
<212> TYPE: PRT
<213> ORGANISM: Artificial Sequence
<220> FEATURE:
<223> OTHER INFORMATION: peptide

<400> SEQUENCE: 14

Phe Thr Tyr Val Arg Phe Asp
 1               5

<210> SEQ ID NO 15
<211> LENGTH: 7
<212> TYPE: PRT
<213> ORGANISM: Artificial Sequence
<220> FEATURE:
<221> NAME/KEY: VARIANT
<222> LOCATION: (5)...(5)
<223> OTHER INFORMATION: "RESIDUE 5 = HIS OR GLN"
<223> OTHER INFORMATION: peptide

<400> SEQUENCE: 15

Pro Val Gln Thr Xaa Gln Ile
 1               5

<210> SEQ ID NO 16
<211> LENGTH: 7
<212> TYPE: PRT
<213> ORGANISM: Artificial Sequence
<220> FEATURE:
<223> OTHER INFORMATION: peptide

<400> SEQUENCE: 16

Glu Leu Thr Phe Val Ile Thr
 1               5
```

```
<210> SEQ ID NO 17
<211> LENGTH: 7
<212> TYPE: PRT
<213> ORGANISM: Artificial Sequence
<220> FEATURE:
<223> OTHER INFORMATION: peptide

<400> SEQUENCE: 17

Met Pro Val Leu Thr Arg Gln
 1               5

<210> SEQ ID NO 18
<211> LENGTH: 7
<212> TYPE: PRT
<213> ORGANISM: Artificial Sequence
<220> FEATURE:
<223> OTHER INFORMATION: peptide

<400> SEQUENCE: 18

Phe Thr Tyr Met Arg Phe Asp
 1               5

<210> SEQ ID NO 19
<211> LENGTH: 7
<212> TYPE: PRT
<213> ORGANISM: Artificial Sequence
<220> FEATURE:
<223> OTHER INFORMATION: peptide

<400> SEQUENCE: 19

Asn Gly Glu Leu Val Pro Gln
 1               5

<210> SEQ ID NO 20
<211> LENGTH: 7
<212> TYPE: PRT
<213> ORGANISM: Artificial Sequence
<220> FEATURE:
<223> OTHER INFORMATION: peptide

<400> SEQUENCE: 20

Cys Thr Pro Thr Gly Arg Val
 1               5

<210> SEQ ID NO 21
<211> LENGTH: 7
<212> TYPE: PRT
<213> ORGANISM: Artificial Sequence
<220> FEATURE:
<221> NAME/KEY: VARIANT
<222> LOCATION: (3)...(3)
<223> OTHER INFORMATION: "RESIDUE 3 = VAL OR ILE"
<220> FEATURE:
<221> NAME/KEY: VARIANT
<222> LOCATION: (5)...(5)
<223> OTHER INFORMATION: "RESIDUE 5 = THR OR PRO"
<223> OTHER INFORMATION: peptide

<400> SEQUENCE: 21

Met Tyr Xaa Pro Xaa Gly Ala
 1               5

<210> SEQ ID NO 22
<211> LENGTH: 7
<212> TYPE: PRT
<213> ORGANISM: Artificial Sequence
<220> FEATURE:
```

```
<223> OTHER INFORMATION: peptide

<400> SEQUENCE: 22

Asn Tyr His Ser Arg Ser Glu
  1               5

<210> SEQ ID NO 23
<211> LENGTH: 7
<212> TYPE: PRT
<213> ORGANISM: Artificial Sequence
<220> FEATURE:
<221> NAME/KEY: VARIANT
<222> LOCATION: (7)...(7)
<223> OTHER INFORMATION: "RESIDUE 7 = LYS OR HIS"
<223> OTHER INFORMATION: peptide

<400> SEQUENCE: 23

Met Gln Thr Arg His Val Xaa
  1               5

<210> SEQ ID NO 24
<211> LENGTH: 6
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: "RESIDUE 1 = CYS OR ASN OR MET"
<223> OTHER INFORMATION: peptide

<400> SEQUENCE: 24

Xaa Phe Tyr Asp Gly Trp
  1               5

<210> SEQ ID NO 25
<211> LENGTH: 7
<212> TYPE: PRT
<213> ORGANISM: Artificial Sequence
<220> FEATURE:
<221> NAME/KEY: VARIANT
<222> LOCATION: (6)...(6)
<223> OTHER INFORMATION: "RESIDUE 6 = ILE OR LEU"
<223> OTHER INFORMATION: peptide

<400> SEQUENCE: 25

Asn Asn Met Gly Thr Xaa Tyr
  1               5

<210> SEQ ID NO 26
<211> LENGTH: 7
<212> TYPE: PRT
<213> ORGANISM: Artificial Sequence
<220> FEATURE:
<223> OTHER INFORMATION: peptide

<400> SEQUENCE: 26

Asn Asn Asn Tyr Val Gly Gln
  1               5

<210> SEQ ID NO 27
<211> LENGTH: 7
<212> TYPE: PRT
<213> ORGANISM: Artificial Sequence
<220> FEATURE:
<223> OTHER INFORMATION: peptide

<400> SEQUENCE: 27

Val Val Asn Ser Tyr Gln Pro
```

<210> SEQ ID NO 28
<211> LENGTH: 7
<212> TYPE: PRT
<213> ORGANISM: Artificial Sequence
<220> FEATURE:
<223> OTHER INFORMATION: peptide

<400> SEQUENCE: 28

Gly Asp Gly Ile Ala Asp Met
1               5

<210> SEQ ID NO 29
<211> LENGTH: 7
<212> TYPE: PRT
<213> ORGANISM: Artificial Sequence
<220> FEATURE:
<223> OTHER INFORMATION: peptide

<400> SEQUENCE: 29

Met Tyr Val Pro Gly Gly Ala
1               5

<210> SEQ ID NO 30
<211> LENGTH: 7
<212> TYPE: PRT
<213> ORGANISM: Artificial Sequence
<220> FEATURE:
<223> OTHER INFORMATION: peptide

<400> SEQUENCE: 30

Ile Asp Gln Thr Val Asn Asn
1               5

<210> SEQ ID NO 31
<211> LENGTH: 7
<212> TYPE: PRT
<213> ORGANISM: Artificial Sequence
<220> FEATURE:
<223> OTHER INFORMATION: peptide

<400> SEQUENCE: 31

Ile Thr Glu Arg Tyr Tyr Thr
1               5

<210> SEQ ID NO 32
<211> LENGTH: 7
<212> TYPE: PRT
<213> ORGANISM: Artificial Sequence
<220> FEATURE:
<223> OTHER INFORMATION: peptide

<400> SEQUENCE: 32

Asp Glu Asn Leu Ile Glu Thr
1               5

<210> SEQ ID NO 33
<211> LENGTH: 7
<212> TYPE: PRT
<213> ORGANISM: Artificial Sequence
<220> FEATURE:
<221> NAME/KEY: VARIANT
<222> LOCATION: (5)...(5)
<223> OTHER INFORMATION: "RESIDUE 5 = ILE OR LEU"
<220> FEATURE:
<221> NAME/KEY: VARIANT
<222> LOCATION: (6)...(6)

```
<223> OTHER INFORMATION: "RESIDUE 6 = MET OR THR"
<223> OTHER INFORMATION: peptide

<400> SEQUENCE: 33

Trp Asp Ile Asp Xaa Xaa Gly
  1               5

<210> SEQ ID NO 34
<211> LENGTH: 7
<212> TYPE: PRT
<213> ORGANISM: Artificial Sequence
<220> FEATURE:
<221> NAME/KEY: VARIANT
<222> LOCATION: (4)...(4)
<223> OTHER INFORMATION: "RESIDUE 4 = ARG OR LYS"
<223> OTHER INFORMATION: peptide

<400> SEQUENCE: 34

Lys His Val Xaa Ala Trp Val
  1               5

<210> SEQ ID NO 35
<211> LENGTH: 7
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: "RESIDUE 2 = LEU OR MET"
<223> OTHER INFORMATION: peptide

<400> SEQUENCE: 35

Lys Xaa Thr Asp Pro Pro Pro
  1               5

<210> SEQ ID NO 36
<211> LENGTH: 7
<212> TYPE: PRT
<213> ORGANISM: Artificial Sequence
<220> FEATURE:
<221> NAME/KEY: VARIANT
<222> LOCATION: (6)...(6)
<223> OTHER INFORMATION: "RESIDUE 6 = MET OR LEU"
<223> OTHER INFORMATION: peptide

<400> SEQUENCE: 36

Met Gly Tyr Ala Gln Xaa Arg
  1               5

<210> SEQ ID NO 37
<211> LENGTH: 7
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: "RESIDUE 2 = THR OR MET"
<223> OTHER INFORMATION: peptide

<400> SEQUENCE: 37

Asp Xaa Pro Val Leu Thr His
  1               5

<210> SEQ ID NO 38
<211> LENGTH: 6
<212> TYPE: PRT
<213> ORGANISM: Artificial Sequence
<220> FEATURE:
<223> OTHER INFORMATION: peptide
```

```
<400> SEQUENCE: 38

Phe Tyr Asp Gly Phe Ala
 1               5

<210> SEQ ID NO 39
<211> LENGTH: 7
<212> TYPE: PRT
<213> ORGANISM: Artificial Sequence
<220> FEATURE:
<223> OTHER INFORMATION: peptide

<400> SEQUENCE: 39

Trp Gln Thr Ala Thr Asn Pro
 1               5

<210> SEQ ID NO 40
<211> LENGTH: 7
<212> TYPE: PRT
<213> ORGANISM: Artificial Sequence
<220> FEATURE:
<223> OTHER INFORMATION: peptide

<400> SEQUENCE: 40

Met Phe Val Pro Pro Gly Ala
 1               5

<210> SEQ ID NO 41
<211> LENGTH: 7
<212> TYPE: PRT
<213> ORGANISM: Artificial Sequence
<220> FEATURE:
<221> NAME/KEY: VARIANT
<222> LOCATION: (4)...(4)
<223> OTHER INFORMATION: "RESIDUE 4 = ARG OR ASN"
<223> OTHER INFORMATION: peptide

<400> SEQUENCE: 41

Asp Trp Gln Xaa Cys Val Trp
 1               5

<210> SEQ ID NO 42
<211> LENGTH: 7
<212> TYPE: PRT
<213> ORGANISM: Artificial Sequence
<220> FEATURE:
<223> OTHER INFORMATION: peptide

<400> SEQUENCE: 42

Asn Arg Asp Leu Leu Val Ser
 1               5

<210> SEQ ID NO 43
<211> LENGTH: 7
<212> TYPE: PRT
<213> ORGANISM: Artificial Sequence
<220> FEATURE:
<223> OTHER INFORMATION: peptide

<400> SEQUENCE: 43

Arg Asp Leu Leu Val Ser Thr
 1               5

<210> SEQ ID NO 44
<211> LENGTH: 7
<212> TYPE: PRT
<213> ORGANISM: Artificial Sequence
```

```
<220> FEATURE:
<223> OTHER INFORMATION: peptide

<400> SEQUENCE: 44

Ala Gln Gly Ser Asp Asn Ile
 1               5

<210> SEQ ID NO 45
<211> LENGTH: 7
<212> TYPE: PRT
<213> ORGANISM: Artificial Sequence
<220> FEATURE:
<223> OTHER INFORMATION: peptide

<400> SEQUENCE: 45

Gly Lys Phe Gly Gln Gln Ser
 1               5

<210> SEQ ID NO 46
<211> LENGTH: 7
<212> TYPE: PRT
<213> ORGANISM: Artificial Sequence
<220> FEATURE:
<223> OTHER INFORMATION: peptide

<400> SEQUENCE: 46

Gly Ala Phe Gly Tyr Gln Ser
 1               5

<210> SEQ ID NO 47
<211> LENGTH: 6
<212> TYPE: PRT
<213> ORGANISM: Artificial Sequence
<220> FEATURE:
<221> NAME/KEY: VARIANT
<222> LOCATION: (5)...(5)
<223> OTHER INFORMATION: "RESIDUE 5 = HIS OR GLN"
<223> OTHER INFORMATION: peptide

<400> SEQUENCE: 47

Gly Arg Phe Gly Xaa Gln
 1               5

<210> SEQ ID NO 48
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 48
gcnccngayt gntgnccraa                                              20

<210> SEQ ID NO 49
<211> LENGTH: 20
<212> TYPE: DNA
<213> ORGANISM: Artificial Sequence
<220> FEATURE:
<221> NAME/KEY: modified_base
<222> LOCATION: (9)...(18)
<223> OTHER INFORMATION: n = inosine
<223> OTHER INFORMATION: primer

<400> SEQUENCE: 49
atgtaygtnc cnccnggngg                                              20
```

<210> SEQ ID NO 50
<211> LENGTH: 21
<212> TYPE: DNA
<213> ORGANISM: Artificial Sequence
<220> FEATURE:
<221> NAME/KEY: modified_base
<222> LOCATION: (3)...(16)
<223> OTHER INFORMATION: n = inosine
<223> OTHER INFORMATION: primer

<400> SEQUENCE: 50
ggngcrttnc cytcgngtcc a                                              21

<210> SEQ ID NO 51
<211> LENGTH: 20
<212> TYPE: DNA
<213> ORGANISM: Artificial Sequence
<220> FEATURE:
<221> NAME/KEY: modified_base
<222> LOCATION: (6)...(18)
<223> OTHER INFORMATION: n = inosine
<223> OTHER INFORMATION: primer

<400> SEQUENCE: 51
tggacngarg gnaaygcncc                                                20

<210> SEQ ID NO 52
<211> LENGTH: 18
<212> TYPE: DNA
<213> ORGANISM: Artificial Sequence
<220> FEATURE:
<221> NAME/KEY: modified_base
<222> LOCATION: (10)...(16)
<223> OTHER INFORMATION: n = inosine
<223> OTHER INFORMATION: primer

<400> SEQUENCE: 52
catrttrttn arngwntt                                                  18

<210> SEQ ID NO 53
<211> LENGTH: 18
<212> TYPE: DNA
<213> ORGANISM: Artificial Sequence
<220> FEATURE:
<221> NAME/KEY: modified_base
<222> LOCATION: (6)...(9)
<223> OTHER INFORMATION: n = inosine
<223> OTHER INFORMATION: primer

<400> SEQUENCE: 53
aanwcnytna ayaayatg                                                  18

<210> SEQ ID NO 54
<211> LENGTH: 20
<212> TYPE: DNA
<213> ORGANISM: Artificial Sequence
<220> FEATURE:
<221> NAME/KEY: modified_base
<222> LOCATION: (8)...(15)
<223> OTHER INFORMATION: n = inosine
<223> OTHER INFORMATION: primer

<400> SEQUENCE: 54
gattgstnnc craangckcc                                                20

<210> SEQ ID NO 55
<211> LENGTH: 20

<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 55
ttnacrtgyt tnggyttraa                                                        20

<210> SEQ ID NO 56
<211> LENGTH: 20
<212> TYPE: DNA
<213> ORGANISM: Artificial Sequence
<220> FEATURE:
<221> NAME/KEY: modified_base
<222> LOCATION: (6)...(18)
<223> OTHER INFORMATION: n = inosine
<223> OTHER INFORMATION: primer

<400> SEQUENCE: 56
acrtgncnng tytgcatngt                                                        20

<210> SEQ ID NO 57
<211> LENGTH: 20
<212> TYPE: DNA
<213> ORGANISM: Artificial Sequence
<220> FEATURE:
<221> NAME/KEY: modified_base
<222> LOCATION: (3)...(18)
<223> OTHER INFORMATION: n = inosine
<223> OTHER INFORMATION: primer

<400> SEQUENCE: 57
gcnatngknm gngtngcnga                                                        20

<210> SEQ ID NO 58
<211> LENGTH: 19
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 58
ccngcnctya ctgcngykg                                                         19

<210> SEQ ID NO 59
<211> LENGTH: 20
<212> TYPE: DNA
<213> ORGANISM: Artificial Sequence
<220> FEATURE:
<221> NAME/KEY: modified_base
<222> LOCATION: (6)...(12)
<223> OTHER INFORMATION: n = inosine
<223> OTHER INFORMATION: primer

<400> SEQUENCE: 59
tcagancnng wntkrtartt                                                        20

<210> SEQ ID NO 60
<211> LENGTH: 20
<212> TYPE: DNA
<213> ORGANISM: Artificial Sequence
<220> FEATURE:
<221> NAME/KEY: modified_base

```
<222> LOCATION: (6)...(12)
<223> OTHER INFORMATION: n = inosine
<223> OTHER INFORMATION: primer

<400> SEQUENCE: 60
tccacngcag tnagwgcwgg                                                    20

<210> SEQ ID NO 61
<211> LENGTH: 17
<212> TYPE: DNA
<213> ORGANISM: Artificial Sequence
<220> FEATURE:
<221> NAME/KEY: modified_base
<222> LOCATION: (6)...(9)
<223> OTHER INFORMATION: n = inosine
<223> OTHER INFORMATION: primer

<400> SEQUENCE: 61
cargtncgna cytcccc                                                       17

<210> SEQ ID NO 62
<211> LENGTH: 20
<212> TYPE: DNA
<213> ORGANISM: Artificial Sequence
<220> FEATURE:
<221> NAME/KEY: modified_base
<222> LOCATION: (3)...(9)
<223> OTHER INFORMATION: n = inosine
<223> OTHER INFORMATION: primer

<400> SEQUENCE: 62
atntgngcnt cytgrttytg                                                    20

<210> SEQ ID NO 63
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 63
ttnacntayg tncgnttyga                                                    20

<210> SEQ ID NO 64
<211> LENGTH: 20
<212> TYPE: DNA
<213> ORGANISM: Artificial Sequence
<220> FEATURE:
<221> NAME/KEY: modified_base
<222> LOCATION: (6)...(15)
<223> OTHER INFORMATION: n = inosine
<223> OTHER INFORMATION: primer

<400> SEQUENCE: 64
atytgntgng tytgnacwgg                                                    20

<210> SEQ ID NO 65
<211> LENGTH: 20
<212> TYPE: DNA
<213> ORGANISM: Artificial Sequence
<220> FEATURE:
<221> NAME/KEY: modified_base
<222> LOCATION: (6)...(15)
<223> OTHER INFORMATION: n = inosine
<223> OTHER INFORMATION: primer
```

```
<400> SEQUENCE: 65
garytnacnt tygtnataac                                           20

<210> SEQ ID NO 66
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 66
tgncgngtya anacnggcat                                           20

<210> SEQ ID NO 67
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 67
ttnacntaya tgcgnttyga                                           20

<210> SEQ ID NO 68
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 68
tgnggnacna gytcnccrtt                                           20

<210> SEQ ID NO 69
<211> LENGTH: 20
<212> TYPE: DNA
<213> ORGANISM: Artificial Sequence
<220> FEATURE:
<221> NAME/KEY: modified_base
<222> LOCATION: (6)...(12)
<223> OTHER INFORMATION: n = inosine
<223> OTHER INFORMATION: primer

<400> SEQUENCE: 69
acyctnccng tnggkgtrca                                           20

<210> SEQ ID NO 70
<211> LENGTH: 20
<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 70
gcnccngkng gnayrtacat                                           20
```

```
<210> SEQ ID NO 71
<211> LENGTH: 20
<212> TYPE: DNA
<213> ORGANISM: Artificial Sequence
<220> FEATURE:
<221> NAME/KEY: modified_base
<222> LOCATION: (3)...(9)
<223> OTHER INFORMATION: n = inosine
<223> OTHER INFORMATION: primer

<400> SEQUENCE: 71
tcnganctng wrtgrtartt                                           20

<210> SEQ ID NO 72
<211> LENGTH: 20
<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 72
tknacrtgnc kngtytgcat                                           20

<210> SEQ ID NO 73
<211> LENGTH: 18
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 73
awnttytayg ayggntgg                                             18

<210> SEQ ID NO 74
<211> LENGTH: 20
<212> TYPE: DNA
<213> ORGANISM: Artificial Sequence
<220> FEATURE:
<221> NAME/KEY: modified_base
<222> LOCATION: (3)...(9)
<223> OTHER INFORMATION: n = inosine
<223> OTHER INFORMATION: primer

<400> SEQUENCE: 74
tananngtnc ccatrttrtt                                           20

<210> SEQ ID NO 75
<211> LENGTH: 20
<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 75
tgnccnacrt anttrttrtt                                           20

<210> SEQ ID NO 76
<211> LENGTH: 20
<212> TYPE: DNA
```

```
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 76
gtngtnaayt sntaycarcc                                               20

<210> SEQ ID NO 77
<211> LENGTH: 21
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 77
ggngayggna tngcngayat g                                             21

<210> SEQ ID NO 78
<211> LENGTH: 20
<212> TYPE: DNA
<213> ORGANISM: Artificial Sequence
<220> FEATURE:
<221> NAME/KEY: modified_base
<222> LOCATION: (9)...(18)
<223> OTHER INFORMATION: n = inosine
<223> OTHER INFORMATION: primer

<400> SEQUENCE: 78
atgtayrtnc cnmcnggngc                                               20

<210> SEQ ID NO 79
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 79
atngaycaya cngtnaayaa                                               20

<210> SEQ ID NO 80
<211> LENGTH: 20
<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 80
atnacngarn gntaytayac                                               20

<210> SEQ ID NO 81
<211> LENGTH: 20
<212> TYPE: DNA
<213> ORGANISM: Artificial Sequence
<220> FEATURE:
<221> NAME/KEY: modified_base
<222> LOCATION: (3)...(15)
```

<223> OTHER INFORMATION: n = inosine
<223> OTHER INFORMATION: primer

<400> SEQUENCE: 81
gangaraayc tnatngarac                                                         20

<210> SEQ ID NO 82
<211> LENGTH: 19
<212> TYPE: DNA
<213> ORGANISM: Artificial Sequence
<220> FEATURE:
<221> NAME/KEY: modified_base
<222> LOCATION: (6)...(12)
<223> OTHER INFORMATION: n = inosine
<223> OTHER INFORMATION: primer

<400> SEQUENCE: 82
cccatnakrt cnatrtccc                                                          19

<210> SEQ ID NO 83
<211> LENGTH: 20
<212> TYPE: DNA
<213> ORGANISM: Artificial Sequence
<220> FEATURE:
<221> NAME/KEY: modified_base
<222> LOCATION: (9)...(15)
<223> OTHER INFORMATION: n = inosine
<223> OTHER INFORMATION: primer

<400> SEQUENCE: 83
aarcaygtna rngcntgggt                                                         20

<210> SEQ ID NO 84
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 84
ggnggnggrt cngtnakytt                                                         20

<210> SEQ ID NO 85
<211> LENGTH: 20
<212> TYPE: DNA
<213> ORGANISM: Artificial Sequence
<220> FEATURE:
<221> NAME/KEY: modified_base
<222> LOCATION: (3)...(15)
<223> OTHER INFORMATION: n = inosine
<223> OTHER INFORMATION: primer

<400> SEQUENCE: 85
cgnakytgng crtancccat                                                         20

<210> SEQ ID NO 86
<211> LENGTH: 20
<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 86
tgngtnagna cnggcrtrtc                                               20

<210> SEQ ID NO 87
<211> LENGTH: 17
<212> TYPE: DNA
<213> ORGANISM: Artificial Sequence
<220> FEATURE:
<221> NAME/KEY: modified_base
<222> LOCATION: (3)...(6)
<223> OTHER INFORMATION: n = inosine
<223> OTHER INFORMATION: primer

<400> SEQUENCE: 87
gcnaanccrt crtaraa                                                  17

<210> SEQ ID NO 88
<211> LENGTH: 20
<212> TYPE: DNA
<213> ORGANISM: Artificial Sequence
<220> FEATURE:
<221> NAME/KEY: modified_base
<222> LOCATION: (6)...(12)
<223> OTHER INFORMATION: n = inosine
<223> OTHER INFORMATION: primer

<400> SEQUENCE: 88
ggrttngtng cngtytgcca                                               20

<210> SEQ ID NO 89
<211> LENGTH: 20
<212> TYPE: DNA
<213> ORGANISM: Artificial Sequence
<220> FEATURE:
<221> NAME/KEY: modified_base
<222> LOCATION: (3)...(12)
<223> OTHER INFORMATION: n = inosine
<223> OTHER INFORMATION: primer

<400> SEQUENCE: 89
gcnccnggng gnacrwacat                                               20

<210> SEQ ID NO 90
<211> LENGTH: 22
<212> TYPE: DNA
<213> ORGANISM: Artificial Sequence
<220> FEATURE:
<221> NAME/KEY: modified_base
<222> LOCATION: (5)...(12)
<223> OTHER INFORMATION: n = inosine
<223> OTHER INFORMATION: primer

<400> SEQUENCE: 90
cccanacrca nntytgccar tc                                            22

<210> SEQ ID NO 91
<211> LENGTH: 20
<212> TYPE: DNA
<213> ORGANISM: Artificial Sequence
<220> FEATURE:
<221> NAME/KEY: modified_base
<222> LOCATION: (6)...(9)
<223> OTHER INFORMATION: n = inosine
<223> OTHER INFORMATION: primer

<400> SEQUENCE: 91
ctyacnanna grtcyctrtt                                               20

```
<210> SEQ ID NO 92
<211> LENGTH: 20
<212> TYPE: DNA
<213> ORGANISM: Artificial Sequence
<220> FEATURE:
<221> NAME/KEY: modified_base
<222> LOCATION: (9)...(12)
<223> OTHER INFORMATION: n = inosine
<223> OTHER INFORMATION: primer

<400> SEQUENCE: 92
gtrctyacna nnagrtcyct                                               20

<210> SEQ ID NO 93
<211> LENGTH: 20
<212> TYPE: DNA
<213> ORGANISM: Artificial Sequence
<220> FEATURE:
<221> NAME/KEY: modified_base
<222> LOCATION: (3)...(11)
<223> OTHER INFORMATION: n = inosine
<223> OTHER INFORMATION: primer

<400> SEQUENCE: 93
atngtrtcns ncccytgsgc                                               20

<210> SEQ ID NO 94
<211> LENGTH: 20
<212> TYPE: DNA
<213> ORGANISM: Artificial Sequence
<220> FEATURE:
<221> NAME/KEY: modified_base
<222> LOCATION: (3)...(9)
<223> OTHER INFORMATION: n = inosine
<223> OTHER INFORMATION: primer

<400> SEQUENCE: 94
gantgytgnc craaytttcc                                               20

<210> SEQ ID NO 95
<211> LENGTH: 20
<212> TYPE: DNA
<213> ORGANISM: Artificial Sequence
<220> FEATURE:
<221> NAME/KEY: modified_base
<222> LOCATION: (8)...(15)
<223> OTHER INFORMATION: n = inosine
<223> OTHER INFORMATION: primer

<400> SEQUENCE: 95
gattgstnnc craangckcc                                               20

<210> SEQ ID NO 96
<211> LENGTH: 18
<212> TYPE: DNA
<213> ORGANISM: Artificial Sequence
<220> FEATURE:
<221> NAME/KEY: modified_base
<222> LOCATION: (7)...(13)
<223> OTHER INFORMATION: n = inosine
<223> OTHER INFORMATION: primer

<400> SEQUENCE: 96
ctgktgnccr aanctscc                                                 18
```

DETECTION AND IDENTIFICATION OF NON-POLIO ENTEROVIRUSES

This application claims benefit of provisional application 60/027,353 Oct. 2, 1996. This application is a 371 of PCT/US97/17734 Oct. 1, 1997.

BACKGROUND OF THE INVENTION

A. Field of the Invention

The invention relates to the detection and classification of pathogenic viruses. In particular, the invention provides diagnostic assays for the detection and classification of enterovirus nucleic acids in biological and other samples.

B. Related Art

Enteroviruses are a heterogeneous group of pathogens responsible for a broad spectrum of human and nonhuman diseases. Enteroviruses belong to a large genus within the family Picornaviridae; other genera within this family include rhinoviruses, hepatoviruses, cardioviruses, and aphthoviruses. The enterovirus genus encompasses polio viruses, coxsackie A viruses (CAV), coxsackie B viruses (CBV), echoviruses, and enteroviruses 68–71, as well as a number of uncharacterized enteroviruses isolated from humans and other primates. (For a review of taxonomy of Picornaviridae see, *VIRUS TAXONOMY: CLASSIFICATION AND NOMENCLATURE OF VIRUSES* Murphy et al., eds. Springer Verlag, 1995).

1. Biological properties of enteroviruses

Like other picornaviruses, enteroviral virions comprise an icosahedral capsid, about 30 nm in diameter, with no envelope, enclosing a core comprising infectious, single-stranded genomic sense RNA, about 7–8.5 kb in size. Enteroviruses are distinguished from other members of the picornaviridae by their stability in acid and their fecal-oral route of passage and transmission. Virus entry into cells is believed to involve specific cellular receptors.

Virion proteins include multiple copies of four capsid proteins (P1 gene products IA, IB, IC, ID such as poliovirus VP4, VP2, VP3, VP1, respectively. A small protein, VPg (Mr about $24 \times 10^3$), is linked covalently to the 5' terminus of the genomic RNA.

The viral genome consists of a ssRNA with a 5' untranslated sequence of variable length followed by an ORF encoding the polyprotein precursor (Mr $240-250 \times 10^3$) to the structural proteins (P1) and the predominantly nonstructural proteins (P2, P3), followed by a short non-coding sequence and a poly (A) tract of variable length. FIG. 1 depicts a generalized enteroviral genome. The filled circle at the 5' end is the genome-linked protein VPg (also referred to as the 3B gene product), followed by, the 5' non-translated region (line). The open boxes depict a long open reading frame encoding a polyprotein that is split to yield the individual proteins mentioned above, followed by the 3' non-translated region (line) and a poly (A) track (angled line). The eventual cleavage products of the polyprotein are indicated by vertical lines in the boxes, the nomenclature of the polypeptides follows an L:4:3:4 scheme corresponding to the genes (numbers) encoded in the L, P1, P2, P3 regions (Rueckert and Wimmer, 1984). The P1 region encodes the structural proteins 1A, 1B, 1C and 1D, usually referred to as VP4, VP2, VP3, and VP1, respectively. VP0, not shown here, is an intermediate precursor for VP4 and VP2. In all viruses, 3C is a protease, in enteroviruses and rhinoviruses 2A is a protease, while in all viruses 3D is considered to be a component of the RNA replicase.

The serotype designations (in parenthesis) of a number of enteroviruses and their genomic sequence accession numbers [in brackets] are:

| | | |
|---|---|---|
| bovine enterovirus 1 | (BEV-1) | [D00214] |
| bovine enterovirus 2 | (BEV-2) | |
| human coxsackievirus A1 to 22 | (CAV-1 to 22) | [D00538] |
| human coxsackievirus A24 | (CAV-24) | |
| human coxsackievirus B I to 6 | (CBV-1 to 6) | [M33854] |
| human echovirus 1 to 7 | (EV-1 to 7) | |
| human echovirus 9 | (EV-9) | |
| human echovirus 11 to 27 | (EV-11 to 27) | |
| human echovirus 29 to 33 | (EV-29 to 33) | |
| human enterovirus 68 to 71 | (HEV68 to 71) | |
| human poliovirus 1 | (HPV-1) | [V01150] |
| human poliovirus 2 | (HPV-2) | |
| human poliovirus 3 | (HPV-3) | |
| porcine enterovirus 1 to 11 | (PEV-1 to 11) | |
| simian enterovirus 1 to 18 | (SEV-1 to 18) | |
| Vilyuisk virus | | |

Sequence identities for different enteroviruses, or between enteroviruses and rhinoviruses are more than 50% over the genome as a whole. Strains within a species often have more than 75% sequence identity over the genome as a whole. Viruses grouped by biological criteria, e.g., the polioviruses, or Coxsackie B viruses, are generally closely related in terms of overall nucleotide sequence identity over the genome as a whole. Different enteroviral serotypes are classified by cross-protection neutralization of infectivity, complement-fixation, specific ELISA using a capture format, or immunodiffusion. Some species can be identified by hemagglutination.

The following is a partial listing of reported correlations between enteroviral species and diseases (Morens, et al., *Textbook of Human Virology*, pp. 427–497, 2nd ed., Mosby-Year Book, St. Louis (1991); Grandien, et al., *Diagnostic Procedures for Viral, Rickettsial and Chlamydial Infections*, pp. 513–569, 6th ed. American Public Health Association, Washington, D.C. (1989)):

| Poliovirus | | | | | | | | | |
|---|---|---|---|---|---|---|---|---|---|
| PV1 | PM | AFP | AM | C* | URI* | | | | |
| PV2 | PM | AFP | AM | C* | URI* | | | | |
| PV3 | PM | AFP | AM | C* | URI* | | | | |

| Coxsackievirus A | | | | | | | | | |
|---|---|---|---|---|---|---|---|---|---|
| CA01 | AM* | ABP* | Ena* | | | | | | |
| CA02 | AFP* | AM* | Enc* | Ena | Ex* | | | | |
| CA03 | AM* | Ena* | | | | | | | |
| CA04 | AFP* | AM* | Enc* | NND* | C* | Ena | HFM* | Ex* | PI* |

-continued

| | | | | | | | | | |
|---|---|---|---|---|---|---|---|---|---|
| CA05 | AM* | Enc* | Ena | HFM* | Ex* | | | | |
| CA06 | AM* | Enc* | Ena | P1* | | | | | |
| CA07 | AFP* | AM* | Ena* | LRI* | | | | | |
| CA08 | AFP* | AM* | Ena | | | | | | |
| CA09 | AFP* | AM | Enc | NND* | ABP* | Ena* | Ex* | P1* | LRI* | Cr |
| CA09var | HFM* | | | | | | | | |
| CA10 | AFP* | AM* | Ena | HFM* | P1* | URI | | | |
| CA11 | AM* | | | | | | | | |
| CA12 | | | | | | | | | |
| CA13 | | | | | | | | | |
| CA14 | AM* | C* | | | | | | | |
| CA15 | | | | | | | | | |
| CA16 | AFP* | AM* | NND* | C* | Ena | HFM | EX* | | |
| CA17 | AM* | | | | | | | | |
| CA18 | AM* | | | | | | | | |
| CA19 | Guillain-Barré | | | | | | | | |
| CA20 | Hep | | | | | | | | |
| CA21 | URI | | | | | | | | |
| CA22 | AM* | Ena* | GI | | | | | | |
| CA24 | AM* | URI | | | | | | | |
| CA24var | AHC | | | | | | | | |
| CB1 | AM | AFP* | Enc* | NND | M | ABP | Ena* | Ex* | P1 | URI* LRI* |
| CB2 | AM | AFP | Enc* | NND | M | ABP | Ena* | Ex* | P1 | URI |
| CB3 | AM | P1 | AFP | Enc* | NND | M | ABP | Ena* | Ex* | P1 URI* |
| CB4 | AM | AFP | Enc* | NND | M | ABP | Ena* | Ex* | P1 | URI* LRI* |
| CB5 | AM | M | AFP | Enc | NND | M | ABP | Ena* | HFM* | Ex* P1 Cr |
| CB6 | AFP* | AM* | P1 | | | | | | |

| Echovirus | | | | | | | | | |
|---|---|---|---|---|---|---|---|---|---|
| E01 | AFP* | AM* | NND* | ABP* | Ex* | P1* | URI | | |
| E02 | AFP* | AM* | Enc* | NND* | Ex* | | | | |
| E03 | AM | AFP | Enc* | NND* | Ena* | Ex* | URI* | | |
| E04 | AM | AFP | Enc* | NND* | C* | Ex* | URI* | | |
| E05 | AM* | NND* | Ex* | | | | | | |
| E06 | AM | AFP | Enc* | NND* | C* | Ena* | Ex* | P1* | URI* |
| E06' | | | | | | | | | |
| E06" | AM | | | | | | | | |
| E07 | AM | AFP* | Enc* | NND* | C* | URI* | | | |
| E08 | ABP* | | | | | | | | |
| E09 | AM | AFP | Enc | NND | C* | ABP* | Ena* | Ex | LRI* |
| E11 | AM | AFP | Enc* | NND | Ex* | P1* | URI* | Cr | |
| E11' | AM | | | | | | | | |
| E12 | | | | | | | | | |
| E13 | AFP* | | | | | | | | |
| E14 | AM* | Enc* | NND | Ex* | | | | | |
| E15 | NND* | | | | | | | | |
| E16 | AFP* | AM* | NND* | Ena* | BE | Ex* | | | |
| E17 | NND* | Ena* | | | | | | | |
| E18 | AFP* | Enc | NND | Ex* | GI | | | | |
| E19 | AM* | AFP* | Enc* | NND | C* | ABP* | Ex* | P1* | URI* GI |
| E20 | AFP* | C* | URI* | | | | | | |
| E21 | NND* | | | | | | | | |
| E22 | AM* | NND | URI* | GI | | | | | |
| E23 | GI | | | | | | | | |
| E24 | AM* | | | | | | | | |
| E25 | Enc* | Ex* | URI* | | | | | | |
| E26 | | | | | | | | | |
| E27 | AM* | | | | | | | | |
| E29 | | | | | | | | | |
| E30 | AFP* | AM* | Ena* | | | | | | |
| E31 | AM* | NND* | | | | | | | |
| E32 | AM | | | | | | | | |
| E33 | AM* | | | | | | | | |
| E34 | GI | | | | | | | | |

| Other enteroviruses | |
|---|---|
| EV68 | LRI* |
| EV69 | |

-continued

| EV70 | AHC | | |
| EV71 | Pa | AM | HFM* |

ABP-acute benign pericarditis, AFP-acute flaccid paralysis, AHC-acute hemorrhagic conjunctivitis, AM-aseptic meningitis, BE-Boston exanthema, C-carditis, Cr-croup, Enc-encephalitis, Ena-enanthema, Ex-exanthema other than BE or HFM, GI-gastrointestinal disease, Hep-hepatitis, HFM-hand-foot-and-mouth disease, LRI-lower respiratory infection, M-myocarditis, NND-neonatal disease, Pe-pericarditis, Pl-pleurodynia, PM-poliomyelitis, Ra-rash, RD-respiratory disease, UF-undifferentiated fever; URI-upper respiratory infection;
*infrequent association.
Other possible associations: nonspecific febrile illness; fatigue syndrome; gastrointestinal disease; hepatitis; diabetes mellitus; pancreatitis; urinary tract infection; arthritis; hemolytic uremic syndrome; orchitis; et al.

Polioviruses (which exist as at least three serotypes) are the most clinically significant of the enteroviruses worldwide, causing paralytic disease in children in developing countries.

Non-polioenteroviruses (NPEV) are also responsible for large numbers of symptomatic and asymptomatic infections each year. Data suggests that there are between 10–15 million illnesses due to NPEV infections each year in the United States (Strikes et al., 1986). NPEVs are responsible for 30,000–50,000 hospitalizations each year for aseptic meningitis, myocarditis, encephalitis, acute hemorrhagic conjunctivitis, nonspecific febrile illnesses, and upper respiratory tract infections (Melnick, Biologicals 21:305–309 (1993)). Certain forms of insulin-dependent diabetes mellitus, affecting an estimated 1 million individuals in the U.S. alone, with 100,000 newly diagnosed each year, may be caused by Cocksackies B4 and B5 virus and echovirus 18. (Wagenknecht et al., Amer. J. Epidem. 133(10):1024–1031 (1991); Frisk et al., J. of Infection 24(1):13–22 (1992).) Enteroviruses are also associated with acute flaccid paralysis: CAVs caused flaccid paralysis in newborn mice, whereas CBV infection in mice resulted in spastic paralysis. Enteroviruses are also associated with dilated cardiomyopathy (Cochrane et al., 1991) and foot and mouth disease. Recent reports have linked NPEV infection with chronic fatigue syndrome (Clements et al. J. Med. Virol. 45:156–161 (1995).

2. Detection of nonpolio enteroviruses

A full catalogue of nonpolio enteroviral serotypes and diseases, and the development of effective treatments for nonpolio enteroviral diseases, are severely limited by the lack of efficient, sensitive diagnostic assays for detecting and classifying enteroviruses. Problem diseases are not detected because there is no quick efficient method for the detection and identification of nonpolio enteroviral infection. Current clinical diagnosis usually relies on medical history and clinical examination. Laboratory methods are based on tissue culture isolation followed by micro-neutralization tests using specific antisera. Each enterovirus generally requires a different array of cell lines. The assays may take weeks and have less sensitivity than biological reagents.

Probe hybridization assays (using either cDNA or RNA probes) have also been used to detect NPEVs (Rotbart et al., *Mol. Cell. Probes* 2:65–73 (1988); Rotbart, *J. Clin. Microbiol.* 28:438–442 (1990); Chapman et al., *J. Clin. Microbiol.* 28:843–850 (1990); differing Hyypiä, et al., *J. Gen. Virol.* 70:3261–3268 (1989); Olive et al., *J. Gen. Virol.* 71:2141–2147 (1990); Gilmaker et al., *J. Med. Virol.* 38:54–61 (1992); Yang et al., *Virus Res.* 24:277–296 (1992); Zoll et al., *J. Clin. Microbiol.* 30:160–165 (1992); Muir et al., *J. Clin. Micro.* 31:31–38 (1993); Drebot et al., *J. Med. Virol.* 44:340–347 (1994); Rotbart et al., *J. Clin. Microbiol.* 32:2590–2592 (1994)). Due to the lack of enteroviral nucleic acid sequence information, most of these probes have targeted the highly conserved 5' non-coding region of the viral genomes. Rotbart, et al., *Human Enterovirus Infections,* pp. 401–418 (1995). First, this region is reportedly very important for the proper translation of the viral genome and second, it is a noncoding region and thus not subject to the degeneracy found in a coding region. Furthermore, RNA probes which target the VP1 capsid region have been used on a limited basis to identify some of the CBVs and a few closely related CAVs (Cova et al., *J. Med. Virol.* 24:11–18 (1988); Alksnis et al., *Mol. Cell. Probes* 3:103:108 (1989); Petitjean et al., *J. Clin. Microbiol.* 28:307–311 (1990)).

None of the published methods for detecting enteroviruses (see a review by Rotbart, et al., *Human Enterovirus Infections, pp.* 401–418 (1995)) can differentiate among the subgroups and serotypes of enteroviruses (i.e., CAV types 1–22, 24; CBV types 1–6, echovirus types 1–9, 11–21, 24–27, 29–33; enteroviruses 68–71). A detection system that identifies and differentiates most or all enterovirus serotypes would improve the speed and accuracy of processing samples and increase the sensitivity of detecting minority populations of enteroviruses in mixed serotype cultures. For example, a prime target in enterovirus diagnosis is to determine their presence, or absence, in newborn infections in order to ascertain whether a meningitis infection is bacterial or viral in nature (Abzug et al., *J. of Pediatrics* 126:447–450 (1995); Rotbart, et al., *Human Enterovirus Infections,* pp. 401–418 (1995)). In addition, rapid and efficient detection and identification of contaminating enteroviruses in vaccine preparations such as polio vaccine preparations is important to ensure the safety of viral vaccines. The present invention addresses these and other concerns.

SUMMARY OF THE INVENTION

The present invention provides methods for detecting and serotyping nonpolio enterovirus (NPEV) nucleic acids in biological samples and in vaccine preparations such as polio vaccines. In one embodiment, the invention provides primers useful for detecting a nonpoliovirus enterovirus. In another embodiment, the invention provides methods for detecting recombinant viral nucleic acids which include nucleic acid sequences from a polio virus and a non-polio enterovirus.

In some embodiments, the invention comprises pairs of primers used to detect the presence or absence of a nonpolio enterovirus in a sample and to identify nonpolio enterovirus serotypes, wherein a first primer of a pair binds to a sense strand of a first nonpolio enterovirus nucleic acid sequence that encodes a first conserved nonpolio enteroviral peptide sequence, and a second primer of the pair binds to an antisense strand of a second nonpolio enterovirus nucleic acid sequence that encodes a second conserved nonpolio enteroviral peptide sequence, wherein both conserved sequences are from a same nonpolio enteroviral protein, to yield an amplification product of a nonpolio enteroviral sequence that encodes both the first and second conserved nonpolio enteroviral peptide sequence.

The methods of the invention also comprise assays for detecting the presence or absence of a nonpolio enterovirus nucleic acid sequence in a sample, comprising contacting the sample with a first and second pair of oligonucleotide primers in an amplification protocol, and determining the presence or absence of a nonpolio enterovirus by detecting for the presence or absence of amplification products.

The methods further comprise detecting recombination between different enteroviruses by contacting a sample suspected of containing an NPEV nucleic acid with a first primer which specifically hybridizes to a conserved sequence in an enteroviral genome and a second primer which specifically hybridizes to a second enteroviral nucleic acid sequence. The presence of an amplified product which is a recombinant viral nucleic acid is then detected.

The methods are performed using samples commonly used for clinical analysis of nucleic acids. A typical sample is a biological sample, such as human serum.

The invention also provides methods for detecting a nonpoliovirus nucleic acid in a vaccine preparation such as a polio vaccine. The methods comprise contacting the vaccine sample with at least two primers which specifically hybridize to NPEV nucleic acid sequences. NPEVs may optionally be detected using gel electrophoresis to identify an amplified fragment that is not present in a control vaccine sample known to contain only poliovirus nucleic acids.

Using 15 complete VP1 sequences, a series of NPEV amplification assay primers were designed to match intervals encoding amino acid sequences within VP1 that are strongly conserved among NPEVS. These primers contain mixed-base and deoxyinosine residues to compensate for the high degeneracy of the targeted codons. Primer sets were identified that code for amino acid sequences which are uniquely conserved among individual groups and serotypes of enteroviruses.

A series of 8 primer sets were preferred for selectively screening for the presence of NPEVs. These degenerate primer sets increase the speed and sensitivity of detecting NPEVs in clinical isolates. Even though no VP1 sequence information was available for the majority (35 out of 49 of enteroviruses tested, surprisingly, 48 out of 49 different enterovirus serotypes could be detected using the methods of the invention.

BRIEF DESCRIPTION OF THE FIGURES

FIG. 2 shows the alignment of corresponding amino acid residues within the VP1 proteins of 15 human enterovirus reference strains. Abbreviations for virus groups are followed by serotype number: CAV, coxsackievirus A; CBV, coxsackievirus B; Echo, echovirus; EV, enterovirus.

FIG. 3 shows the specific amplification of selected NPEVs representing each major NPEV group with the primers listed in Table 1. Clarified lysates of infected cell cultures (1 µl/reaction) were the source of templates for a polymerase chain reaction ("PCR") protocol. After 30 amplification cycles, DNA products were separated by electrophoresis on polyacrylamide gels and visualized by ethidium bromide staining. The presence of an amplification product with the predicted size is indicated by a plus sign (+) in the appropriate column for each isolate.

FIG. 4 shows the selected primer sets that were tested against a collection of 49 NPEVS. The samples were analyzed as described in FIG. 3. The presence of a PCR product, corresponding to the correct size for each different primer set, is indicated with a plus sign. PCR reactions yielding either no product, or a product of incorrect size are indicated with minus signs.

Figure 1:
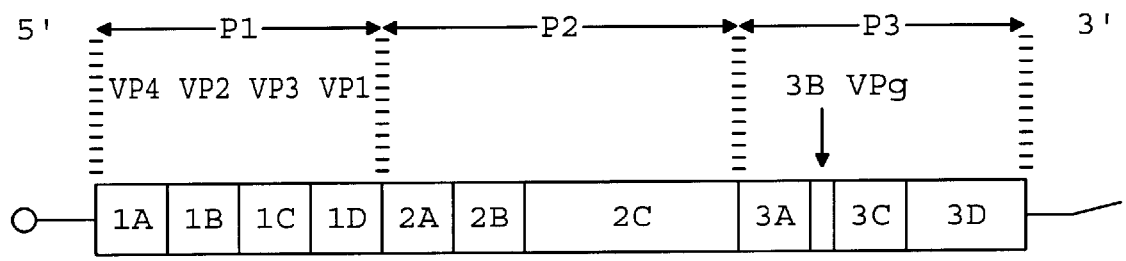
FIG. 1 shows the genome structure and gene organization of enteroviruses. The filled circle at the 5' end is the genome-linked protein VPg (also referred to as the 3B gene product), followed by the 5' non-translated region (5' NTR; solid line). The open box depicts the long ORF encoding the polyprotein that is followed by the 3' non-translated region (line) and a poly (A) track (angled line). The eventual cleavage products of the polyprotein are indicated by vertical lines in the boxes. The P1 region encodes the structural proteins VP4, VP2, VP3, and VP1, (also referred to as 1A, 1B, 1C and 1D, respectively.)

The results from FIG. 4 are summarized in FIG. 5. After analysis with the selected primer sets, samples can be quickly screened by comparing to this chart. This information gives you the most likely serotype or group of serotypes which may be present in the sample. Further screening, using conventional micro-neutralization tests, can then be performed on only those suspected serotypes. This will significantly reduce the number of micro-neutralization tests that need to be done, thus speeding up identification by eliminating unnecessary testing and conserving the limited amounts of Melnick antisera pools that are available.

DETAILED DESCRIPTION OF THE INVENTION

A. Definitions

The terms "hybridize(s) specifically" or "specifically hybridize(s)" refer to complementary hybridization between an oligonucleotide (e.g., a primer or labeled probe) and a target sequence. The term specifically embraces minor mismatches that can be accommodated by reducing the stringency of the hybridization media to achieve the desired priming for the PCR polymerases or detection of hybridization signal.

The term "biological sample" refers to a sample comprising any biological material (e.g., biological fluids) containing nucleic acids. Biological samples will typically comprise whole blood, serum, urine, saliva, cerebrospinal fluid, semen, and the like.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but tropically ranges from about 10 to about 30 nucleotides. Short primer molecules generally require cooler temperatures to form sufficiently stable hybrid complexes with the template. A primer need not reflect the exact sequence of the template but must be sufficiently complementary to specifically hybridize with a template. The term primer, when directed to a sequence that encodes a defined peptide sequence, specifically encompasses degenerate primers designed to identify conserved amino acid residues, in which the third position of either (one or more) selected or all codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). When primer pairs are referred to herein, the pair is meant to include one primer which is capable of hybridizing to the sense strand of a double-stranded target nucleic acid (the "sense primer") and one primer which is capable of hybridizing to the antisense strand of a double-stranded target nucleic acid (the "antisense primer").

"Probe" refers to an oligonucleotide which binds through complementary base pairing to a subsequence of a target nucleic acid. A primer may be a probe. It will be understood by one of skill in the art that probes will typically substantially bind target sequences lacking complete complementarity with the probe sequence depending upon the stringency of the hybridization conditions. The probes are typically directly labelled (e.g., with isotopes or fluorescent moieties) or indirectly labelled such as with biotin to which a streptavidin complex may later bind. By assaying for the presence or absence of the probe, one can detect the presence or absence of the target.

A "sequence specific to" a particular virus species or strain (e.g., poliovirus) is a sequence unique to the species or strain, (that is, not shared by other previously characterized species or strains). A probe or primer containing a sequence complementary to a sequence specific to a virus will typically not hybridize to the corresponding portion of the genome of other viruses under stringent conditions (e.g., washing the solid support in 2×SSC, 0.1% SDS at 70° C.).

The phrase "conserved nonpolio enteroviral peptide sequence" means that a peptide sequence is specific for at least two nonpoliovirus enteroviral sequences, and is present on the corresponding protein of at least two different nonpolio enteroviruses. "A same nonpolio enteroviral protein" means that the conserved nonpolio enteroviral peptide sequences to which the primer pairs specifically hybridize are present on a same protein (e.g., VPg, the polyprotein precursor, VP4, VP2, VP3, VP1, the 2A non-structural protein) of at least one nonpolio enterovirus.

"Amplification protocol" means an assay for amplifying a nucleic acid sequence, such as a PCR assay, a ligase chain reaction assay (LCR), Qβ-replicase amplification, transcription amplification, and self-sustained sequence replication.

The phrase "bracket a nucleic acid sequence" means that primers that bind to opposite strands of a DNA molecule are so disposed that a polymerase chain reaction replicates the nucleic acid sequence between the two primer binding sites.

The term "substantially identical" indicates that two or more nucleotide sequences share a majority of their sequence. Generally, this will be at least about 66% of their sequence and preferably about 95% of their sequence. Another indication that sequences are substantially identical is if they hybridize to the same nucleotide sequence, preferably under stringent conditions (see, e.g., Sambrook et al., *Molecular Cloning—A Laboratory Manual,* Cold Spring Harbor Laboratory, Cold Spring Harbor, New York, 1985). Stringent conditions are sequence-dependent and will be different in different circumstances. Generally, stringent conditions are selected to be about 5° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 60° C.

B. The invention

The present invention is directed to the detection of nucleic acids derived from non-polioenteroviruses (NPEV). In particular, the invention provides sensitive methods (e.g., the polymerase chain reaction, PCR) for detecting NPEV and recombinant viruses potentially derived from polio vaccines.

Nucleotide sequences of various enteroviruses are available in the scientific literature and in databases such as GenBank (National Center for Biotechnology Information, Natl. Library of Medicine, National Institutes of Health, 8600 Rockville Pike, Bethesda, Md. 20894). For instance, sequences of poliovirus types 1, 2 and 3 are disclosed in Toyoda et al., *J. Mol Biol* 174: 561–585, (1984). Sequences of NPEVs (e.g., VP1 nucleic acid and peptide sequences) are reported at the following Accession Nos. CAV2-L28146, CAV9-D00627, CAV16-U05876, CAV21-D00538, CAV24-D90457, CBV1-M16560, CBV3-M33854, CBV4-X05690, CBVS-X67706, EV70-D00820, EV71-U22521, Echo 6-U05851, Echo 9-XB4981, Echo 11-X80059, Echo 12-X77708 Brown and Fallansch (1995), *Virus Res.* 39:195–205

Molecular reagents targeting capsid sequences should give identifications that correlate better with the most important biological properties of the virus (e.g., receptor specificity, serotype) than would reagents targeting other regions. However, the lack of a sequence database for most of the NPEVs in the VP1 region has led to a lack of methods targeting this area of the genome. Another factor contributing to this lack of methods is that there can be a wide nucleotide sequence variation (even between members of the same serotype). This high degree of nucleotide sequence diversity among enteroviruses is exacerbated by the evidence that polioviruses undergo frequent recombination (Cammack et al., *Virology* 167:507–514 (1989); Furione et al., *Virology* 196:199–208 (1993); Lipskaya et al., *J. Med. Virol.* 35:290–296 (1991); Rico-Hesse et al., *Virology* 160:311–322 (1987); Zheng et al., *J. Infect. Dis.* 168:1361–1367 (1993)); genetic exchange may place poliovirus capsid sequences into genetic backgrounds derived from other polioviruses (Kew et al., *New Aspects of Positive-Strain RNA Viruses,* pp. 357–365, American Society of Microbiology, Washington, D.C. (1990); King et al., *Nucleic Acids Res.* 16:11705–11723 (1988); Zheng et al., *J. Infect. Dis.* 168:1361–1367 (1993)) or possible NPEVs (Furione et al., *Virology* 196:199–208 (1993)). Similar recombination and genetic exchange is suspected for many of the NPEVS, but direct evidence is lacking.

To address these problems, very specific PCR primer pairs that, as a group, can identify almost all NPEV serotypes are provided below. This is achieved by targeting highly conserved amino acid regions and by using degenerate primers.

1. PCR amplification assays

A number of amplifiction protocols may be used, but a polymerase chain reaction ("PCR") is preferred. As noted above, the primers of the invention are typically used in PCR amplification of the target nucleic acid. The PCR process is well known in the art and is thus only briefly described herein. For a review of PCR methods and protocols, see, e.g., U.S. Pat. Nos. 4,683,195; 4,683,202; 4,965,188; and Innis, et al., eds. *PCR Protocols. A Guide to Methods and Application* (Academic Press, Inc., San Diego, Calif. 1990), each of which is incorporated herein by reference. PCR reagents and protocols are also available from commercial vendors, such as Roche Molecular Systems.

Because enteroviruses are RNA viruses, the first step in the amplification is the synthesis of a DNA copy (cDNA) of the region to be amplified. Reverse transcription can be carried out as a separate step, or in a homogeneous reverse transcription-polymerase chain reaction (RT-PCR), a modification of the polymerase chain reaction for amplifying RNA. Methods suitable for PCR amplification of enterovirus nucleic acids are described in Romero and Rotbart in *Diagnostic Molecular Biology: Principles and Applications* pp.401–406, Persing et al. eds., (Mayo Foundation, Rochester, Minn. 1993); Rotbart et al. U.S. Pat. No. 5,075, 212 and Egger et al., *J. Clin. Microbiol.* 33:1442–1447 (1995)).

The primers used in the methods of the invention are preferably at least about 15 nucleotides to about 50 nucleotides in length, more preferably from about 15 nucleotides to about 30 nucleotides in length. If a probe is used to detect the amplification product, the primers are selected from parts of the viral genomes that are upstream and downstream from the probe.

Preferably, the primers target the sense or antisense strands of nucleotide sequences that encode particular conserved regions. Particular combinations of groups of primer pairs yield a matrix of amplification products that is used to detect and serotype nonpolio enteroviruses present in a sample. A preferred combination is one comprising the following primer pairs (described in greater below):
5S/6A (SEQ ID NO:49/SEQ ID NO:50),
7S/9A (SEQ ID NO:53/SEQ ID NO:55),
14S/11A (SEQ ID NO:57/SEQ ID NO:56),
51S/52A (SEQ ID NO:73/SEQ ID NO:74),
61S/68A (SEQ ID NO:78/SEQ ID NO:84),
64S/65A (SEQ ID NO:81/SEQ ID NO:82),
67S/1A (SEQ ID NO:83/SEQ ID NO:48), and
67S/8A (SEQ ID NO:83/SEQ ID NO:54).

To amplify a target nucleic acid sequence in a sample by PCR, the sequence must be accessible to the components of the amplification system. In general, this accessibility is ensured by isolating the nucleic acids from the sample. A variety of techniques for extracting nucleic acids, in particular ribonucleic acids, from biological samples are known in the art. Alternatively, if the sample is fairly readily disruptable, the nucleic acid need not be purified prior to amplification by the PCR technique, i.e., if the sample is comprised of cells, particularly peripheral blood lymphocytes or monocytes, lysis and dispersion of the intracellular components may be accomplished merely by suspending the cells in hypotonic buffer.

The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for a sufficient time to cause the denaturation of the duplex but not to cause an irreversible denaturation of the polymerase (see U.S. Pat. No. 4,965, 188). Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In the present invention, the initial template for primer extension is typically RNA. Reverse transcriptases (RTs) suitable for synthesizing a cDNA from the RNA template are well known. For example, *Thermus thermophilus* (Tth) DNA polymerase, a thermostable DNA polymerase with reverse transcriptase activity is marketed by Roche Molecular Systems (Alameda, Calif.).

PCR is most usually carried out as an automated process with a thermostable enzyme. In this process, the temperature of the reaction mixture is cycled through a denaturing region, a primer annealing region, and an extension reaction region automatically. Equipment specifically adapted for this purpose is commercially available from Roche Molecular Systems.

2. Alternate amplification assays

As described above, a preferred embodiment of the invention incorporates RT-PCR amplification. One of skill will recognize, however, that amplification of target sequences in a sample may be accomplished by any known method, such as ligase chain reaction (LCR), Qβ-replicase amplification, transcription amplification, and self-sustained sequence replication, each of which provides sufficient amplification.

3. Detection of amplification products

As explained in detail below, the size of the amplified fragments (the "amplification products") produced by the methods of the invention is typically sufficient to distinguish polioviruses from either NPEV or poliovirus recombinants. Thus, in some embodiments of the invention, size fractionation (e.g., gel electrophoresis) of the amplified fragments produced in a given sample can be used to distinguish poliovirus from other viruses of interest. This is typically carried out by amplifying a control containing known viruses (e.g., isolated poliovirus) with the same primers used to amplify the sample of interest. After running the amplified sequences in an agarose gel and labeling with ethidium bromide according to well known techniques (see, Sambrook et al.), the pattern of bands in the sample and control are compared. The presence of different or additional bands in the sample as compared to the control, is an indication of the presence of NPEV or poliovirus recombinants.

Alternatively, the amplification products of the invention can be detected using oligonucleotide probes specific to the target nucleic acids. The probes are usually selected from regions of the genome of the NPEV or poliovirus that are specific to one or the other.

Sequence-specific probe hybridization is a well known method of detecting desired nucleic acids in a sample. Under sufficiently stringent hybridization conditions, the probes hybridize specifically only to substantially complementary sequences. The stringency of the hybridization conditions can be relaxed to tolerate varying amounts of sequence mismatch. Detection of the amplified product utilizes this sequence-specific hybridization to insure detection of only the correct amplified target, thereby decreasing the chance of a false positive caused by the presence of homologous sequences from related organisms or other contaminating sequences.

A number of hybridization formats well known in the art, including but not limited to, solution phase, solid phase, mixed phase, or in situ hybridization assays. In solution (or liquid) phase hybridizations, both the target nucleic acid and the probe or primer are free to interact in the reaction mixture. In solid phase hybridization assays, either the target or probes are linked to a solid support where they are available for hybridization with complementary nucleic acids in solution. Exemplary solid phase formats include Southern hybridizations, dot blots, and the like.

The hybridization complexes are detected according to well known techniques; such detection is not a critical aspect of the present invention. Nucleic acid probes capable of specifically hybridizing to a target can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include ligands which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers of the invention can be synthesized and labeled using well known techniques. Oligonucleotides for use as probes and primers may be chemically synthesized according to the solid phase phosphoramidite triester method first described by Beaucage, S. L. and Caruthers, M. H., 1981, Tetrahedron Letts., 22(20) :1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

4. Diagnosis of enteroviral conditions and diseases

The above described primers and assays are used to detect nonpolio enteroviruses in a sample, to serotype these viruses, to diagnose enteroviral diseases and medical conditions, and to correlate (or disprove a correlation between) specific symptoms or combinations of symptoms with the presence of a particular enterovirus. Diagnostic applications are supplemented and confirmed by an examination of the medical history and profile of the individual tested. Nonpolio enteroviral diseases, medical conditions and symptoms that are diagnosed by the methods of the invention encompass all diseases, medical conditions and symptoms reported to be associated with nonpolio enteroviruses here and in the scientific literature, specifically including aseptic meningitis, enteroviral diabetes mellitus, enteroviral conjunctivitis, acute flaccid paralysis, acute benign pericarditis, exanthema, enanthema, dilated cardiomyopathy, foot and mouth disease, chronic fatigue syndrome, febrile illnesses, and upper respiratory tract infections. The detection of nonpolio enteroviral infections and their correlation with medical conditions will make possible vaccines and methods of treatment.

5. Kits

The present invention also provide kits, multicontainer units comprising components useful for practicing the present method. A useful kit can contain probes for detecting the desired target nucleic acid, from either a recombinant virus or an NPEV. In some cases, the probes may be fixed to an appropriate support membrane. The kit will also contain primers provided in this invention. Other optional components of the kit include, for example, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. In addition to the above components, the kit can also contain instructions for carrying out the method of this invention.

EXAMPLES

A. Materials and Methods

Viruses:

Euterovirus isolates were identified by neutralization pools of immune sera (Melnick, *Virology*, pp. 549–605, 2nd ed., Raven Press, N.Y. (1990)) followed by confirmation of serotype with monotype neutralizing polyclonal antibodies. Viruses were propagated in HeLa or RD monolayers to produce high-titer inoculation stocks.

Amino acid sequences:

All of the VP1 amino acid sequences in FIG. 2 were obtained from Genbank. Their accession numbers are as follows: CAV2-L28146, CAV9-D00627, CAV16-U05876, CAV21-D00538, CAV24-D90457, CBV1-M16560, CBV3-M33854, CBV4-X05690, CBV5-X67706, EV70-D00820, EV71-U22521, Echo 6-U05851, Echo 9-X84981, Echo 11-X80059, Echo 12-X77708. Brown and Fallansch (1995), *Virus Res.* 39:195–205.

Oligonucleotide synthesis:

Synthetic oligodeoxynucleotides were prepared, purified, and analyzed as described (Yang et al., *Virus Res.* 20:159–179 (1991)). The degenerate primers used for virus amplification are listed in Table 1. Each NPEV, whose amino acid sequence in FIG. 1 provided the source of the targeted amino acids, is identified along with the numbers in parentheses indicating the genomic intervals matching these amino acids.

PCR amplification and analysis:

In vitro amplification by PCR was performed as described previously (Kilpatrick et al., *J. Clin. Micro.* (December 1996)). Amplification reactions were carried out in 50 µl reaction mixtures containing 1 µl of each individual virus tissue culture lysate in 50 mM Tris-HCl (pH 8.3), 70 mM KCl, 5 mM MgCl2, 10 mM dithiothreitol, 80 pmol of each degenerate primer, 200 µM each of dATP, dCTP, dGTP, dTTP (Pharmacia), 0.5% NP-40, 5 U placenta ribonuclease inhibitor (Boehringer Mannheim Biochemicals, Indianapolis, Ind.), 1.25 U AMV reverse transcriptase (Boehringer Mannheim), and 1.25 U of Taq DNA polymerase (Perkin Elmer-Cetus, Norwalk, Conn.). The reaction mixtures were prepared, excluding the ribonuclease inhibitor, Amv reverse transcriptase, and Taq DNA polymerase, overlaid with mineral oil, heated for 5 min at 95° C. to release the virion RNA and chilled on ice. The enzymes were then added and the samples incubated at 42° C. for 30 min before 30 cycles of programmed amplification (denaturation:94° C., 1 min; annealing: 42° C., 1 min; extension: 60° C., 1 min) in a DNA thermal cycler (Perkin Elmer-Cetus). Conditions for polyacrylamide gel electrophoresis, and detection of amplified products by ethidium bromide staining were as described (Yang et al., *Virus Res.* 20:159–179 (1991)).

Selection of primer binding sites

The VP1 sequence information for 15 prototype NPEVs is shown in FIG. 2. VP1 sequences for the approximately 50 remaining NPEVs have not been determined.

Several areas of amino acid conservation were identified in FIG. 2. The conserved sequences were then used to generate a series of primers which could be used in amplification reactions to detect enteroviral serotypes. A representative list of peptide target sequences and primer sequences is depicted in Table 1.

TABLE 1

NPEV PCR PRIMERS

| PRIMER* | TARGETED PEPTIDE SEQUENCE** | DEGENERATE PRIMER SEQUENCE*** |
|---|---|---|
| 1A | FGQQSGA (3–9)[2-CBV-1] | 5'-GCICCIGAYTGITGICCRAA |
| 5S | MYVPPGG (142–148)[1] | 5'-ATGTAYGTICCICCIGGIGG |
| 6A | WTEGNAP (169–175)[1] | 5'-GGIGCRTTICCYTCIGTCCA |
| 6S | WTEGNAP (169–175)[1] | 5'-TGGACIGARGGIAAYGCICC |
| 7A | N(ts)LNNM (208–213)[1] | 5'-CATRTTRTTIARIGWITT |
| 7S | N(ts)LNNM (208–213)[1] | 5'-AAIWCIYTIAAYAAYATG |
| 8A | GATG(yq)QS (1–7)[2-CBV-1] | 5'-GATTGSTIICCRAAIGCKCC |
| 9A | FKPKHVK (237–243)[1] | 5'-TTIACRTGYTTIGGYTTRAA |
| 11A | TMQTRHV (47–53)[1] | 5'-ACRTGICIIGTYTGCATIGT |
| 14S | A(mi)(gv)RVAD (10–16)[1] | 5'-GCIATIGKIMGIGTIGCIGA |
| 24S | PALTA(av)E (42–48)[1] | 5'-CCIGCICTYACTGCIGYKG |
| 25A | NY(kh)(st)RSE (63–69)[3] | 5'-TCAGAICIIGWITKRTARTT |
| 27A | PALTAVE (42–48)[1] | 5'-TCCACIGCAGTIAGWGCWGG |
| 28A | GEVRNQ (143–148)[3] | 5'-CARGTICGIACYTCCCC |
| 33A | QNQDAQI | 5'-ATITGIGCITCYTGRTTYTG |
| 34S | FTYVRFD (107–113)[4] | 5'-TTIACITAYGTICGITTYGA |
| 35A | PVQT(hq)QI (135–141)[1] | 5'-ATYTGITGIGTYTGIACWGG |
| 36S | ELTFVIT (115–121)[1] | 5'-GARYTIACITTYGTIATAAC |
| 38A | MPVLTRQ (73–79)[5] | 5'-TGICGIGTYAAIACIGGCAT |
| 39S | FTYMRFD (107–113)[6] | 5'-TTIACITAYATGCGITTYGA |
| 40A | NGELVPQ (143–149)[6] | 5'-TGIGGIACIAGYTCICCRTT |
| 41A | CTPTGRV (140–146)[7] | 5'-ACYCTICCIGTIGGKGTRCA |
| 43A | MY(vi)P(tp)GA (153–159)[3] | 5'-GCICCIGKIGGIAYRTACAT |
| 46A | NYHSRSE (55–61)[1] | 5'-TCIGAICTIGWIITGRTARTT |
| 47A | MQTRHV(kh) (48–54)[1] | 5'-TKIACRTGICKIGTYTGCAT |
| 51S | (cnm)FYDGW (191–196)[1] | 5'-AWITTYTAYGAYGGITGG |
| 52A | NNMGT(il)Y (211–217)[1] | 5'-TAIAIIGTICCCATRTTRTT |
| 54A | NNNYVGQ (255–261)[8] | 5'-TGICCIACRTAITTRTTRTT |
| 55S | VVNSYQP (215–221)[8] | 5'-GTIGTIAAYTSITAYCARCC |
| 59S | GDGIADM (1–7)[6] | 5'-GGIGAYGGIATIGCIGAYATG |
| 61S | MYVPGGA (153–159)[3] | 5'-ATGTAYRTICCIMCIGGIGC |
| 62S | IDQTVNN | 5'-ATIGAYCAYACIGTIAAYAA |
| 63S | ITERYYT (140–146)[9] | 5'-ATIACIGARIGITAYTAYAC |
| 64S | DENLIET (60–66)[6] | 5'-GAIGARAAYCTIATIGARAC |
| 65A | WDID(il)(mt)G (109–115)[6] | 5'-CCCATIAKRTCIATRTCCC |
| 67S | KHV(rk)AWV (140–146)[1] | 5'-AARCAYGTIARIGCITGGGT |
| 68A | K(lm)TDPPP (182–188)[1] | 5'-GGIGGIGGRTCIGTIAKYTT |
| 69A | MGYAQ(ml)R (114–120)[6] | 5'-CGIAKYTGIGCRTAICCCAT |
| 73A | D(tm)PVLTH (136–142)[10] | 5'-TGIGTIAGIACIGGCRTRTC |
| 74A | FYDGFA (203–208)[1] | 5'-GCIAAICCRTCRTARAA |
| 76A | WQTATNP (181–187)[6] | 5'-GGRTTIGTIGCIGTYTGCCA |
| 77A | MFVPPGA (164–160)[7] | 5'GCICCIGGIGGIACRWACAT |
| 78A | DWQ(rn)CVW (30–36)[2-CBV-B3] | 5'-CCCAIACRCAIITYTGCCARTC |
| 79A | NRDLLVS (37–43)[2-CAV-9] | 5'-CTYACIAIIAGRTCYCTRTT |
| 80A | RDLLVST (38–44)[2-ECH-12] | 5'-GTRCTYACIAIIAGRTCYCT |
| 81A | AQGSDNI (45–51)[2-CAV-24] | 5'-ATIGTRTCISICCCYTGSGC |
| 82A | GKFGQQS (1–6)[2-CAV-16] | 5'-GAITGYTGICCRAAYTTTCC |
| 83A | GAFGYQS (1–6)[2-ECH-11] | 5'-GATTGSTIICCRAAIGCKCC |
| 84A | GRFG(hq)Q (3–9)[2-CAV-2] | 5'-CTGKTGICCRAAICTSCC |

*A = antisense, S = sense
**All amino acid residues (with corresponding position numbers) are located in VP1, with the exception of #2- which is located in the 2A nonstructural protein and are from the following isolates:
1 = CBV-B1; 2 = CBV-B1; 3 = CAV-A21; 4 = CBV-B3; 5 = CAV-A9; 6 = CAV-A16; 7 = EV71; 8 = EV70; 9 = CAV-A24; 10 = echovirus 12; 11 = Rhinovirus II
***(Mixed base residues are as follows: Y = both T and C; R = A and G; M = A & C; K = G & T; S = G & C; W = A & T; I = deoxyinosine)

To complement all possible codon combinations the selected primer sites, the primers of the present invention contain either mixed-base residues or, preferably, deoxyinosine residues at degenerate codon positions. Deoxyinosine residues, which can pair with all four bases (Martin et al., *Nucleic Acids Res.* 13:8927–8938 (1985); Ohtsuka et al., *J. Biol. Chem.* 260:2605–2608 (1985); Rossolini et al., *Mol. Cell. Probes* 8:91–98 (1994)) were incorporated into the primers to match those positions having possible four-fold degeneracy.

The following is a partial list of possible primer pairs:
5S/6A (SEQ ID NO:49/SEQ ID NO:50),
5S/74A (SEQ ID NO:49/SEQ ID NO:87),
6S/7A (SEQ ID NO:51/SEQ ID NO:52),
7S/8A (SEQ ID NO:53/SEQ ID NO:54),
7S/9A (SEQ ID NO:53/SEQ ID NO:55),
14S/11A (SEQ ID NO:57/SEQ ID NO:56),
24S/47A (SEQ ID NO:58/SEQ ID NO:72),
24S/25A (SEQ ID NO:58/SEQ ID NO:59),
24S/46A (SEQ ID NO:58/SEQ ID NO:71),
34S/28A (SEQ ID NO:63/SEQ ID NO:61),
34S/33A (SEQ ID NO:63/SEQ ID NO:62), 34S/35A (SEQ ID NO:63/SEQ ID NO:64),
34S/38A (SEQ ID NO:63/SEQ ID NO:66),
34S/73A (SEQ ID NO:63/SEQ ID NO:86),
36S/35A (SEQ ID NO:65/SEQ ID NO:64),
39S/40A (SEQ ID NO:67/SEQ ID NO:68),
39S/41A (SEQ ID NO:67/SEQ ID NO:69),
39S/52A (SEQ ID NO:73/SEQ ID NO:74),
55S/54A (SEQ ID NO:76/SEQ ID NO:75),
59S/27A (SEQ ID NO:77/SEQ ID NO:60),
61S/68A (SEQ ID NO:78/SEQ ID NO:84),
62S/27A (SEQ ID NO:79/SEQ ID NO:60),
63S/43A (SEQ ID NO:79/SEQ ID NO:70),
64S/69A (SEQ ID NO:81/SEQ ID NO:85),
64S/65A (SEQ ID NO:81/SEQ ID NO:82),
67S/1A (SEQ ID NO:83/SEQ ID NO:48), and
67S/8A (SEQ ID NO:83/SEQ ID NO:54).

One example of how the information of FIG. 2 was used to select primer pairs is shown by the degenerate primer pair 5S/6A. The sense primer 5S targets the amino acids MYVP-PGG (a.a. # 142–148 in CBV1, for example). This amino acid sequence is highly conserved in all known NPEVS. In addition, Palmenburg, *Molecular Aspects of Picornavirus Infection and Detection,* pp. 215–230, American Society of Microbiology (1989) showed this amino acid sequence is highly conserved among polioviruses and rhinoviruses as well. The antisense primer 6A is the selective primer in the amplification reaction and recognizes the amino acids WTEGNAP (a.a. # 169–175 in CBVI, for example). This primer is uniquely conserved primarily among CBVs and those NPEVs closely related to CBVS, such as CAV9, and all four sequenced echoviruses (FIG. 2).

The fact that the 5S/6A primer set also appears to recognize CAV9 is not unexpected. Other researchers have shown, using sequence alignment programs, that CAV9 is very closely related to CBVs (Pulli et al., *Virology,* in press (1995)). Many other conserved amino acid epitopes (6–7 residues in length) were identified and are listed in Table 1 along with their relative position within VPI and their corresponding degenerate PCR primer.

Some primers were designed to recognize more than 1 amino acid at a particular residue and are indicated by parentheses around that residue in Table 1. For example, primer 7S (which codes for the peptide sequence N(ts) LNNM) was designed to recognize nucleotides which code for either a threonine residue (found in CBVI) or a serine residue (found in CBV4) in the second amino acid position of the primer. As a result, the synthesis of this primer results in several species of 23 primers with one-half of the primer species containing TGI residues (which encodes for Serine) and the other one-half containing AGI residues (which encodes for Threonine) in positions 4, 5, and 6, respectively.

Some of the other group-specific primer pairs include 51S/52A, which recognizes all known CBV isolates. In this case, the sense primer 51S is the selective primer in the amplification reaction with the "FYDGW" amino acid sequence being specific for CBVs and closely related serotypes such as many of the echoviruses, while excluding CAVs from amplification. On the other hand, primers 61S/68A and 64S/65A were designed using CAV16 known sequences to target CAVs in general.

B. Amplification of enterovirus templates

In order to determine if all of the isolates tested in this report contain amplifiable viral templates, these isolates were first tested with PCR primers (data not shown) which recognize all enteroviruses (Yang et al., *Virus Res.* 20:159–179 (1991)). Each of the primers listed in Table 1 were initially tested on a panel of viruses representing major NPEV groups (including CAV9, 12, 21, CBV1–6, echoviruses 41 11, 30, and EV71). The results from screening this virus panel, shown in FIG. 3, were used to determine how conserved the targeted amino acid sites were among this selected virus group.

Sequence analysis of the PCR products amplified from templates of several viruses (for example the 101 bp amplification product from the 5S/6A primer set) confirmed that the primers had primed specific amplification of the targeted nucleotide interval (data not shown). General patterns of reactivity can be determined from these results. In particular, primer sets 5S/6A, 7S/9A, 14S/11A, and 51S/52A were found to be broadly reactive with both CBVs and echoviruses. This amplification pattern agrees with the method, discussed above, that was used to select these particular primer sites. The amino acids for these four primer sets are shown to be conserved throughout the CBVs as well as the echoviruses in FIG. 2.

The four antisense primer sequences (i.e. primers 6A, 9A, 11A and 52A) are not seen in the known CAV sequences shown in FIG. 2. This explains why there is no amplification when these primers are used on CAV isolates (with the noted exception of CAV9).

Many of the remaining primers tested in FIG. 3 reacted with either a few virus isolates, or none at all. Primer sets that were either broadly reactive or selective in amplification were further tested using a larger panel of prototype NPEVS.

C. NPEV PCR primer pool.

A collection of 49 NPEVs was assembled for further PCR analysis. The bulk of NPEVs not found in this collection consists of CAVs, which grow very poorly in cell culture (Muir et al., *J. Clin. Micro.* 31:31–38 (1993); Rotbart, et al., *Human Enterovirus Infections,* pp. 401–418 (1995)).

This expanded virus panel was tested with PCR primer sets identified in FIG. 3. Primers 5S/6A, 7S/9A, 14S/11A and 51S/52A were found to be broadly reactive through all CBVs and most of the echoviruses (FIG. 4). Primer set 67S/SA was shown to amplify selected echoviruses (EC11, 12, 17, 19, 21, 24, 29, and 31) without reacting with CAVs and CBVs. The 67S/1A primer set reacted with a few CAVs (A3 & A8) and several echoviruses (EC9, 11, 12, 13, 17, 21, 24, 29, and 31). EV69 was also amplified by 67S/1A. The primer sets 61S/68A and 64S/65A amplified the predicted PCR product size with only CAVs (A3, A4, A5, A6, A8, A10, A16 for 61S/68A and A8, A10, A14, A16 for 64S/65A), as well as those viruses closely related to CAVs, i.e. EV70 and EV71. The 8 PCR primer sets identified in FIG. 4 can be used as a collection or "pool" of primer sets for rapidly performing a preliminary screen against suspected NPEV isolates.

A quick screen chart was assembled using these primers to aid in the screening of NPEVs (FIG. 5). This chart also shows that none of these primers reacted with CAV12, 21, 24 and did not detect EV68. Other PCR results shown in FIG. 3 specifically detect either CAV12 (39S/40A) or CAV21 (34S/28A). Primers, 63S/43A, specifically detect CAV24 (data not shown). Only one NPEV, EV68, was not amplified by PCR primers in this report. Twelve of the isolates can be specifically identified using this primer pool (i.e. CAV3, 8, 14, EC9, 11, 13, 14, 17, 19, 24, 31, and EV69). However, until an extensive sequence database for all prototype NPEVs can be assembled by sequencing the PCR products in this report, all virus isolates yielding positive PCR reactions (i.e., amplification products of the correct size for each primer set), should be serotyped using monospecific antisera in micro-neutralization tests, if at all possible. By first using these PCR primers to quickly screen virus isolates (within 1 day), one can concentrate on performing micro-neutralization tests with only those monospecific antisera suggested by the PCR results.

PCR assays using the degenerate panPV/PCR primers were positive for a very diverse sample of poliovirus genotypes, had excellent diagnostic specificities, and had template sensitivities comparable to those obtained with non-degenerate primers. Similar PCR primer designs should be directly applicable to the detection of NPEVS.

Amino acid sequences seen in a particular group or serotype can be specifically targeted using degenerate PCR primers, providing that the targeted amino acids are truly unique to that group or serotype. Either sense or antisense primers can provide the selectivity, with the remaining primer in the reaction having a broader reactivity to other viruses not in the targeted group.

Since NPEVs consist of positive sense, single strand RNA, it is preferred to have an antisense selective primer since this primer will be responsible for the initial cDNA synthesis, thus initially amplifying only the targeted sequences. The majority of primers in Table 1 which were used for specific template amplifications use the antisense primer for the selectivity of the reaction, such as the 6A, 9A, 11A and 52A primers which have a broad reactivity against CBvs and echoviruses. However, several sense-polarity primers are also used for specific selection.

For example, the sense primer 59S targets the amino acid sequence unique to CAV16 (GDGIADM) and therefore amplifies only CAV16 despite the fact that the antisense primer 27A (which is complementary to the sequence that encodes the peptide PALTAVE) targets a widely conserved site found in almost all enteroviruses. In another case, the sense primer 63S targets the amino acids unique to CAV24 (ITERYYT) and therefore amplifies only CAV24, even though the 43A primer (MYVPPPGA) in this set targets an epitope that is widely conserved among all enteroviruses.

The identification of such conserved amino acid epitopes allowed us to design specific PCR primers that could identify 97% of the NPEVs in our collection.

Using these primers sets together (as shown in FIG. 5) for preliminary screening provides a powerful tool in identifying NPEVS. The use of PCR to perform preliminary screens for NPEVS should speed the identification of virus isolates by reducing the numbers of micro-neutralization assays that need to be performed. Also, PCR with degenerate primers has been shown to detect as little as 100 fg of polivovirus RNA (Kilpatrick, et al., *J. Clin. Micro.* (published in December 1996)). Similar sensitivities should be expected for detecting NPEV serotypes.

The RNAs from 48 out of a total 49 different prototype NPEVs used for testing were detected by PCR. Even though the nucleic acid sequences within VPI for the majority of these NPEVs (35/49) were unknown prior to testing, these isolates were detected due to the high amino acid conservation in the targeted epitopes.

Now that specific PCR primers have been identified which can amplify within the VP1 gene of almost all NPEVs (48/49 tested), sequence databases can be established which will yield even more type-specific sequences. These nucleotide sequences will be the targets for even more specific molecular reagents (i.e. primers and probes) which will further increase the speed, efficiency, and accuracy of future NPEV identification.

All publications, patents and patent applications mentioned in this specification are hereby incorporated by reference for all purposes into the specification to the same extent as if each individual publication, patent or patent application had been specifically and individually indicated to be incorporated by reference. Although the foregoing invention has been described in some detail by way of illustration and example for purposes of clarity of understanding, it will be obvious that certain changes and modifications may be practiced within the scope of the appended claims. For instance, primers that specifically hybridize to 5' nontranslated region of an enteroviral genome or to other enteroviral proteins may be used. In another embodiment, the present invention contemplates assays wherein the primer pairs disclosed above are combined with primer pairs that recognize other viral species. For example, patent publication Ser. No. 95/02704, and U.S. patent applications Ser. Nos. 08/092,110 and 08/273,474 (incorporated by reference herein) describe primers that specifically detect polioviruses. In addition, primers 85A and 86S target known rhinoviruses (which are also in the Picornavirus family) and would be very useful in differentiating between upper respiratory infections that are caused by rhinoviruses, and repiratory infections caused by members of the enterovirus group.

| PRIMER | TARGETED PEPTIDE SEQUENCE | DEGENERATE PRIMER SEQUENCE |
| --- | --- | --- |
| 85A | QPED(av)IE (46–52)[II-RH1-2] | 5'-TCRATIITRTCYTCIGGYTG |
| 86S | NPVE(nh)YI (1–7)[II-RHI-2] | 5'-AAICCIGTYGARIAYTAYAT |

What is claimed is:

1. A method for detecting and serotyping non-polio enteroviruses in a biological sample, said method comprising (1) contacting a first portion of the sample with a first pair of primers in a first amplification protocol, wherein the first pair of primers have an associated first characteristic amplification product if certain non-polio enteroviruses are present in the sample;

(2) determining whether or not the first characteristic amplification product is present;

(3) contacting a second portion of the sample with a second pair of primers in a second amplification protocol, wherein the second pair of primers have an associated second characteristic amplification product if certain non-polio enteroviruses are present in the sample and wherein the second pair of primers are different from the first pair of primers;

(4) determining whether or not the second characteristic amplification product is present;

(5) based on whether or not the first and second characteristic amplification product are present, selecting one or more subsequent pair of primers and contacting the one or more subsequent pair of primers with additional portions of the sample in subsequent amplification protocols, wherein each subsequent pair of primers is different from each pair of primers already used and wherein each subsequent pair of primers has an associated subsequent characteristic amplification product if certain non-polio enteroviruses are present in the sample;

(6) determining whether or not the associated characteristic amplification product for each subsequent pair of primers used is present;

(7) repeating steps 5 and 6 for one or more subsequent pairs of primers if the non-polio enterviruses cannot be serotyped based on the determinations of steps 2, 4, and 6 until the non-polio enterviruses can be serotyped, wherein the one or more subsequent pairs of primers are different from all pairs of primers used in earlier amplification protocols; and (8) determining the serotype or groups of serotypes of the non-polio entervirus that may be present in the sample;

wherein the first, second, and any subsequent pairs of primers are independently selected from the group consisting of
(a) 5S/6A (SEQ ID NO:49/SEQ ID NO:50),
(b) 7S/9A (SEQ ID NO:53/SEQ ID NO:55),
(c) 14S/11A (SEQ ID NO:57/SEQ ID NO:56),
(d) 51S/52A (SEQ ID NO:73/SEQ ID NO:74),
(e) 61S/68A (SEQ ID NO:78/SEQ ID NO:84),
(f) 64S/65A (SEQ ID NO:81/SEQ ID NO:82),
(g) 67S/1A (SEQ ID NO:83/SEQ ID NO:48), and
(h) 67S/8A (SEQ ID NO:83/SEQ ID NO:54);
and wherein each pair of primers may only be selected and subjected to an amplification protocol once.

2. The method as defined in claim 1, wherein the sample is a biological fluid.

3. The method as defined in claim 2, wherein the sample is human whole blood, serum, urine, salvia, cerebrospinal fluid, or semen.

4. The method as defined in claim 2, wherein the first, second, and any subsequent amplification protocols are polymerase chain reactions or reverse-transcription polymerase chain reactions.

5. The method as defined in claim 2, wherein the detecting and serotyping of the non-polio enteroviruses in the biological sample is used to diagnose enteroviral diseases or medical conditions.

6. The method as defined in claim 3, wherein the detecting and serotyping of the non-polio enteroviruses in the biological sample is used to diagnose enteroviral diseases or medical conditions.

7. The method as defined in claim 5, wherein the detecting and serotyping of the non-polio enteroviruses in the biological sample is used to diagnose enteroviral diseases or medical conditions.

8. The method as defined in claim 6, wherein the enteroviral diseases or medical conditions are aseptic meningitis, enteroviral diabetes mellitus, enteroviral conjunctivitis, acute flaccid paralysis, acute benign pericarditis, exanthema, enanthema, dilated cardiomyopathy, foot and mouth disease, chronic fatigue syndrome, febrile illnesses, or upper respiratory tract infections.

9. The method as defined in claim 5, wherein the biological sample is a vaccine.

10. The method as defined in claim 5, wherein the biological sample is a polio vaccine.

11. The method as defined in claim 1, further comprising subjecting the sample to micro-neutralization tests or monotype neutralizing antibodies appropriate for the serotype or groups of serotypes determined in step 8.

12. Oligonucleotide primers which can be used to detect and serotype non-polio enteroviruses in a sample using an amplification protocol, said primers comprising at least two sets of primer pairs independently selected from the group consisting of:
(a) 5S/6A (SEQ ID NO:49/SEQ ID NO:50),
(b) 7S/9A (SEQ ID NO:53/SEQ ID NO:55),
(c) 14S/11A (SEQ ID NO:57/SEQ ID NO:56),
(d) 51S/52A (SEQ ID NO:73/SEQ ID NO:74),
(e) 61S/68A (SEQ ID NO;78/SEQ ID NO:84),
(f) 64S/65A (SEQ ID NO:81/SEQ ID NO:82),
(g) 67S/1A (SEQ ID NO83/SEQ ID NO:48), and
(h) 67S/8A (SEQ ID NO:83/SEQ ID NO:54).

13. The oligonucleotide primers as defined in claim 12, wherein the amplification protocol is polymerase chain reaction or reverse-transcription polymerase chain reaction.

* * * * *